US010881283B2

(12) United States Patent
Tabata et al.

(10) Patent No.: US 10,881,283 B2
(45) Date of Patent: Jan. 5, 2021

(54) ENDOSCOPE APPARATUS

(71) Applicant: OLYMPUS CORPORATION, Tokyo (JP)

(72) Inventors: Motoki Tabata, Hino (JP); Bakusui Daidoji, Hachioji (JP); Takeshi Ito, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 341 days.

(21) Appl. No.: 16/009,730

(22) Filed: Jun. 15, 2018

(65) Prior Publication Data

US 2018/0289246 A1 Oct. 11, 2018

Related U.S. Application Data

(63) Continuation of application No. PCT/JP2015/085357, filed on Dec. 17, 2015.

(51) Int. Cl.
*A61B 1/00* (2006.01)
*A61B 1/06* (2006.01)
(Continued)

(52) U.S. Cl.
CPC .......... *A61B 1/0638* (2013.01); *A61B 1/0005* (2013.01); *A61B 1/00009* (2013.01);
(Continued)

(58) Field of Classification Search
None
See application file for complete search history.

(56) References Cited

U.S. PATENT DOCUMENTS

| 2003/0139650 A1* | 7/2003 | Homma | A61B 1/0638 |
| | | | 600/181 |
| 2012/0010465 A1* | 1/2012 | Erikawa | A61B 1/0669 |
| | | | 600/109 |
| 2016/0331218 A1 | 11/2016 | Kamee et al. | |

FOREIGN PATENT DOCUMENTS

| JP | 2006341075 A | 12/2006 |
| JP | 2011218135 A | 11/2011 |

(Continued)

OTHER PUBLICATIONS

Chinese Office Action dated Aug. 21, 2019 in Chinese Patent Application No. 201580085440.4.
(Continued)

*Primary Examiner* — Timothy J Neal
(74) *Attorney, Agent, or Firm* — Scully, Scott, Murphy & Presser, P.C.

(57) ABSTRACT

An endoscope apparatus includes an imager configured to detect reflected and scattered light of illumination light radiated to an observation object and output an imaging signal, the illumination light including light in three wavelength ranges corresponding to first, second, and third depth regions, and an image processor including an intermediate emphasis image generator configured to generate an intermediate emphasis image, based on a first emphasis image signal generated based on emphasis narrowband light, a first non-emphasis image signal generated based on non-emphasis narrowband, and image signals corresponding to all wavelength ranges not including the first emphasis and non-emphasis image signals, and a display image generator configured to generate a display image based on the intermediate emphasis image.

23 Claims, 14 Drawing Sheets

(51) Int. Cl.
*A61B 1/04* (2006.01)
*A61B 1/07* (2006.01)
*A61B 5/145* (2006.01)
*A61B 5/1455* (2006.01)
*A61B 5/1459* (2006.01)

(52) U.S. Cl.
CPC ............... *A61B 1/04* (2013.01); *A61B 1/043* (2013.01); *A61B 1/063* (2013.01); *A61B 1/0646* (2013.01); *A61B 1/0669* (2013.01); *A61B 1/0684* (2013.01); *A61B 1/07* (2013.01); *A61B 5/1459* (2013.01); *A61B 5/14546* (2013.01); *A61B 5/14556* (2013.01)

(56) References Cited

FOREIGN PATENT DOCUMENTS

| | | |
|---|---|---|
| JP | 2012152413 A | 8/2012 |
| JP | 2013005981 A | 1/2013 |
| JP | 2014061152 A | 4/2014 |
| JP | 2015054191 A | 3/2015 |
| WO | 2015/115320 A1 | 8/2015 |

OTHER PUBLICATIONS

International Preliminary Report and Written Opinion dated Jun. 28, 2018 received in PCT/JP20151085357.
International Search Report dated Mar. 15, 2016 issued in PCT/JP2015/085357.
Japanese Office Action dated Jan. 28, 2020 in Japanese Patent Application No. 2017-555946.
Japanese Office Action dated Jun. 18, 2019 in Japanese Patent Application No. 2017-555946.
Japanese Office Action dated Apr. 7, 2020 in Japanese Patent Application No. 2017-555946.
Japanese Office Action dated Oct. 29, 2019 in Japanese Patent Application No. 2017-555946.

* cited by examiner

|  | Subframe | Subframe | Subframe | Subframe | Subframe | Subframe |
|---|---|---|---|---|---|---|
| Laser 1 (415nm) | ON | — | — | ON | — | — |
| Laser 2 (445nm) | — | — | — | — | — | — |
| Laser 3 (540nm) | — | — | — | — | — | — |
| Laser 4 (515nm) | — | ON | — | — | ON | — |
| Laser 5 (595nm) | — | — | — | — | — | — |
| Laser 6 (635nm) | — | — | ON | — | — | ON |

FIG. 9

| Color image | Selectable image | Use laser |
|---|---|---|
| B image | Primary image 1 (emphasis image of superficial layer) | Laser 1(415nm) |
| | Primary image 2 (non-emphasis image of superficial layer) | Laser 2(445nm) |
| G image | Primary image 3 (emphasis image of intermediate layer) | Laser 3(540nm) |
| | Primary image 4 (non-emphasis image of intermediate layer) | Laser 4(515nm) |
| R image | Primary image 5 (emphasis image of deep layer) | Laser 5(595nm) |
| | Primary image 6 (non-emphasis image of deep layer) | Laser 6(635nm) |

FIG. 11

| | One frame | | | | One frame | | | |
|---|---|---|---|---|---|---|---|---|
| | Subframe | Subframe | Subframe | Subframe | Subframe | Subframe | Subframe | Subframe |
| Laser 1 (415nm) | ON | — | — | — | ON | — | — | — |
| Laser 2 (445nm) | — | — | — | — | — | — | — | — |
| Laser 3 (540nm) | — | ON | — | — | — | ON | — | — |
| Laser 4 (515nm) | — | — | ON | — | — | — | ON | — |
| Laser 5 (595nm) | — | — | — | — | — | — | — | — |
| Laser 6 (635nm) | — | — | — | ON | — | — | — | ON |

FIG. 12

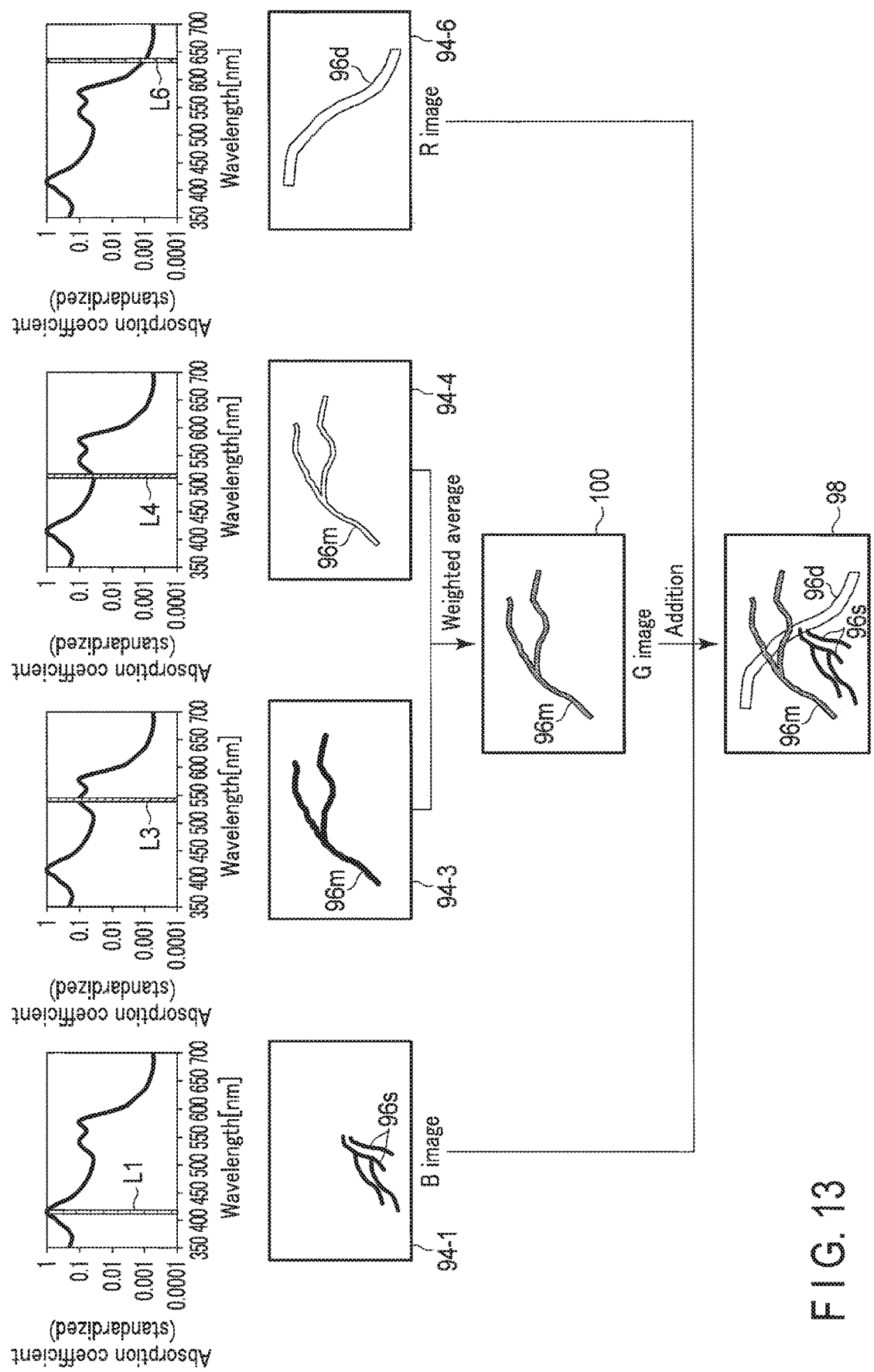
F.I.G. 13

| Color image | Selectable image | Use laser |
|---|---|---|
| B image | Primary image 1 (emphasis image of superficial layer) | Laser 1(415nm) |
| | Primary image 2 (non-emphasis image of superficial layer) | Laser 2(445nm) |
| | Primary intermediate emphasis image of superficial layer (primary image 1 and primary image 2 are synthesized) | Laser 1(415nm) Laser 2(445nm) |
| G image | Primary image 3 (emphasis image of intermediate layer) | Laser 3(540nm) |
| | Primary image 4 (non-emphasis image of intermediate layer) | Laser 4(515nm) |
| | Primary intermediate emphasis image of intermediate layer (primary image 3 and primary image 4 are synthesized) | Laser 3(540nm) Laser 4(515nm) |
| R image | Primary image 5 (emphasis image of deep layer) | Laser 5(595nm) |
| | Primary image 6 (non-emphasis image of deep layer) | Laser 6(635nm) |
| | Primary intermediate emphasis image of deep layer (primary image 5 and primary image 6 are synthesized) | Laser 5(595nm) Laser 6(635nm) |

F I G. 15

| | Laser 1 (415nm) | Laser 2 (445nm) | Laser 3 (540nm) | Laser 4 (515nm) | Laser 5 (595nm) | Laser 6 (635nm) |
|---|---|---|---|---|---|---|
| M1 | ○ | — | — | ○ | — | ○ |
| M2 | — | ○ | ○ | — | — | ○ |
| M3 | — | ○ | — | ○ | ○ | — |
| M4 | ○ | — | ○ | ○ | — | ○ |
| M5 | ○ | ○ | ○ | — | — | ○ |
| M6 | ○ | — | — | ○ | ○ | ○ |
| M7 | ○ | ○ | — | ○ | ○ | — |
| M8 | — | ○ | ○ | — | ○ | ○ |
| M9 | — | ○ | ○ | ○ | ○ | — |
| M10 | ○ | — | ○ | ○ | ○ | ○ |
| M11 | — | ○ | ○ | ○ | ○ | ○ |
| M12 | ○ | ○ | ○ | — | ○ | ○ |
| M13 | ○ | ○ | — | ○ | ○ | ○ |
| M14 | ○ | ○ | ○ | ○ | ○ | — |
| M15 | ○ | ○ | ○ | ○ | — | ○ |
| M16 | ○ | ○ | ○ | ○ | ○ | ○ |

FIG. 16

| | Subframe | Subframe | Subframe | Subframe | Subframe | Subframe | Subframe | Subframe | Subframe | Subframe | Subframe | Subframe |
|---|---|---|---|---|---|---|---|---|---|---|---|---|
| | One frame | | | | | | One frame | | | | | |
| Laser 1 (415nm) | ON | — | — | — | — | — | — | — | — | — | — | — |
| Laser 2 (445nm) | — | ON | — | — | — | — | — | — | — | — | — | — |
| Laser 3 (540nm) | — | — | ON | — | — | — | — | — | ON | — | — | — |
| Laser 4 (515nm) | — | — | — | ON | — | — | — | — | — | ON | — | — |
| Laser 5 (595nm) | — | — | — | — | ON | — | — | — | — | — | ON | — |
| Laser 6 (635nm) | — | — | — | — | — | ON | — | ON | — | — | — | ON |

F I G. 17

ENDOSCOPE APPARATUS

CROSS-REFERENCE TO RELATED APPLICATIONS

This application is a Continuation application of PCT Application No. PCT/JP2015/085357, filed Dec. 17, 2015, the entire contents of which are incorporated herein by reference.

BACKGROUND OF THE INVENTION

1. Field of the Invention

The present invention relates to an endoscope apparatus capable of highlighting a diagnosis target substance present in an observation object.

2. Description of the Related Art

For example, Jpn. Pat. Appln. KOKAI Publication No. 2014-61152 discloses an endoscope apparatus capable of highlighting blood vessels of an observation object. The endoscope apparatus includes blood vessel emphasis filters that transmit wavelength ranges of 405 to 425 nm and 530 to 550 nm for broadband light, the wavelength ranges having a high absorption coefficient for hemoglobin that is a diagnosis target substance present in the observation object, as illumination light for emphasizing the blood vessels. An image signal in which the contrast of superficial blood vessels is high by blue narrowband light of 405 to 425 nm and the contrast of intermediate and deep blood vessels is high by green narrowband light of 530 to 550 nm, of blood vessel emphasis illumination light that is the illumination light transmitted through the blood vessel emphasis filters, is obtained.

Therefore, the superficial blood vessels and the intermediate and deep blood vessels can be highlighted by the blue narrowband light of 405 to 425 nm and the green narrowband light of 530 to 550 nm.

BRIEF SUMMARY OF THE INVENTION

An endoscope apparatus includes an imager configured to detect reflected and scattered light of illumination light radiated to an observation object and output an imaging signal, the illumination light including light in three wavelength ranges corresponding to first, second, and third depth regions deferent from each other, and an image processor configured to generate a display image from the imaging signal. The image processor includes an intermediate emphasis image generator configured to generate an intermediate emphasis image in which the degree of emphasis of a diagnosis target substance is between emphasis and non-emphasis, based on, in the imaging signal, a first emphasis image signal generated based on emphasis narrowband light included in an emphasis wavelength range that emphasizes the diagnosis target substance existing in the observation object, a first non-emphasis image signal generated based on non-emphasis narrowband included in a non-emphasis wavelength range not including the emphasis wavelength range, and image signals corresponding to all wavelength ranges not including the first emphasis image signal and the first non-emphasis image signal, in the three wavelength ranges, and a display image generator configured to generate the display image based on the intermediate emphasis image.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9 is a table illustrating an example of laser light source lighting timing/imaging signal acquisition in a superficial blood vessel emphasis mode.

FIG. 11 is a table illustrating a combination pattern of BGR images for specific layer emphasis image acquisition.

FIG. 12 is a table illustrating an example of laser light source lighting timing/imaging signal acquisition in a superficial blood vessel emphasis-intermediate blood vessel intermediate emphasis mode.

FIG. 13 is a diagram schematically illustrating a flow of display image generation in the superficial blood vessel emphasis-intermediate blood vessel intermediate emphasis mode.

FIG. 15 is a table illustrating a combination pattern of BGR images including intermediate emphasis.

FIG. 16 is a table illustrating a combination of laser light sources to be used in each emphasis mode.

FIG. 17 is a table illustrating another example of laser light source lighting timing/imaging signal acquisition.

DESCRIPTION OF EMBODIMENTS

Hereinafter, embodiments for implementing the present invention will be described with reference to the drawings.

Figure 1:
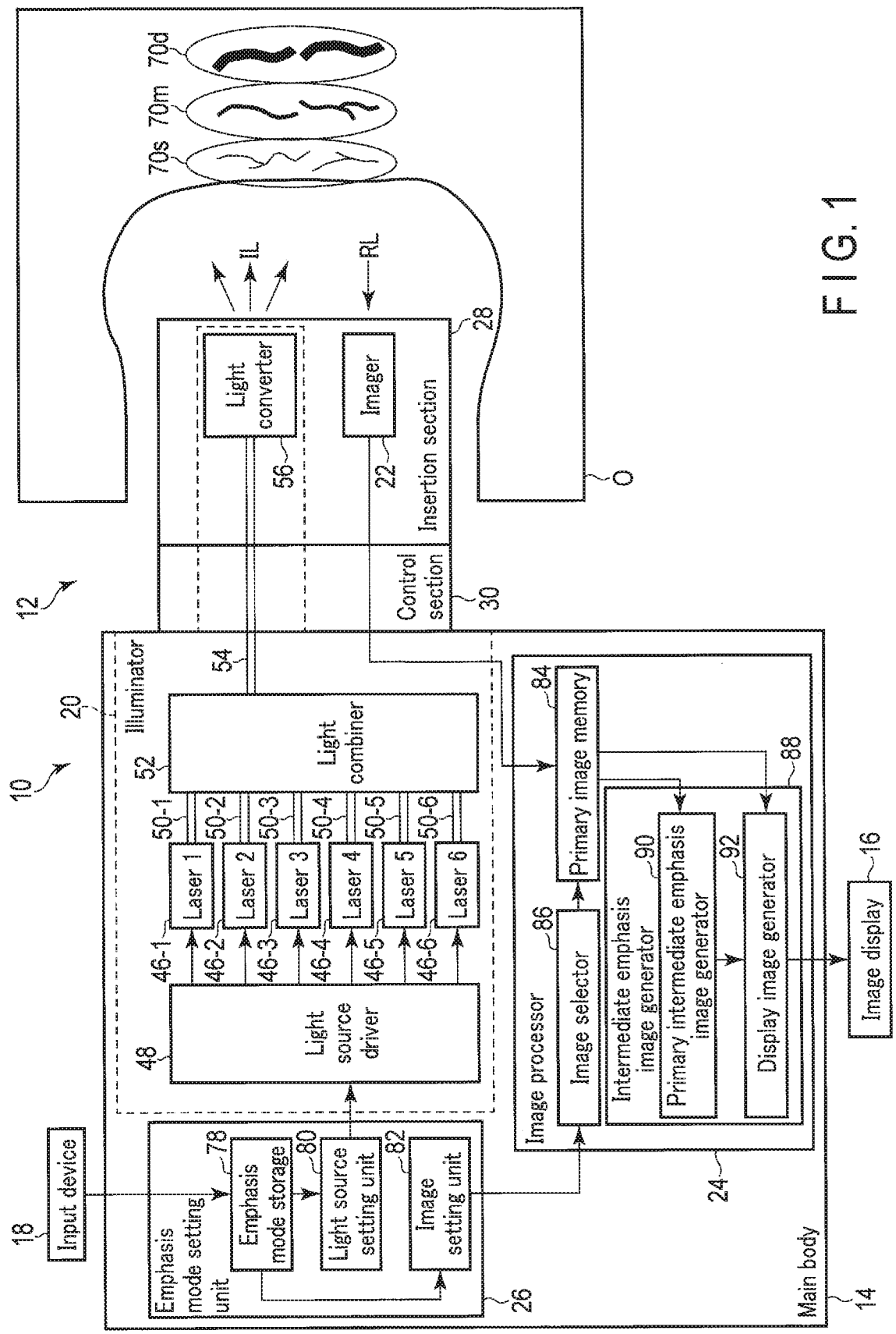
FIG. 1 is a block diagram illustrating a schematic configuration of an endoscope apparatus according to an embodiment of the present invention.
Figure 2:
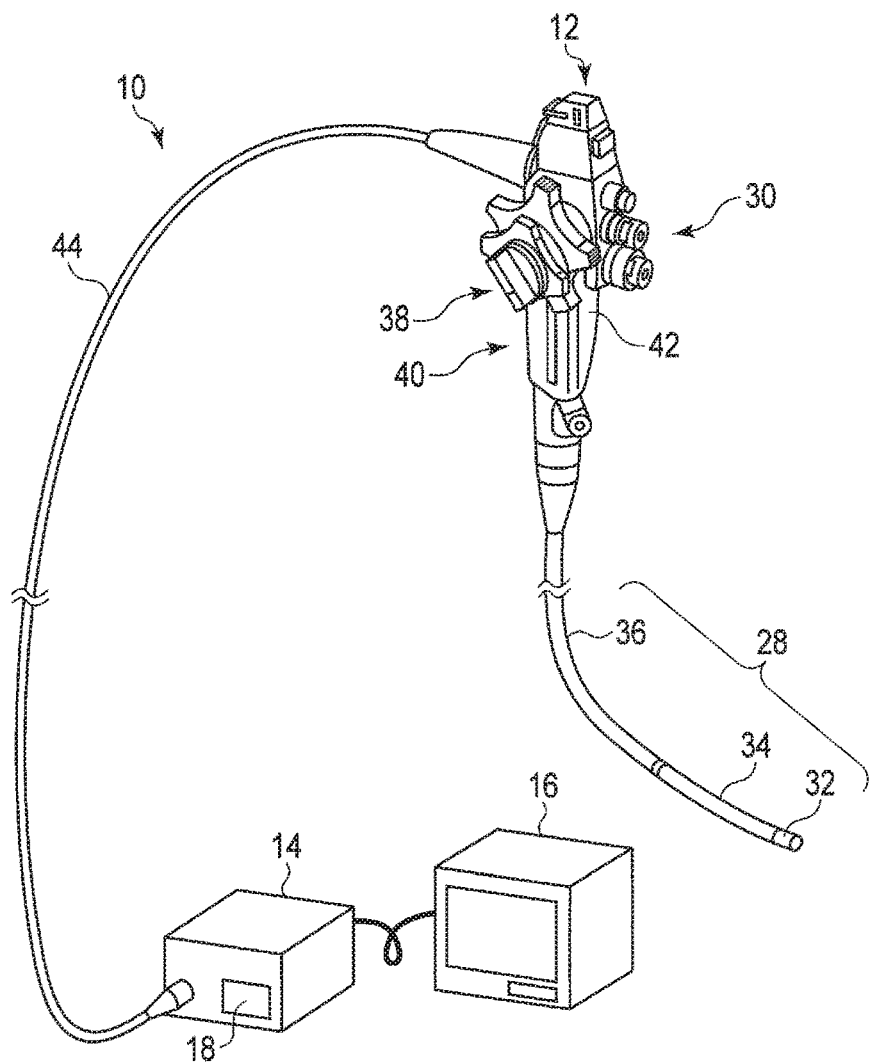
FIG. 2 is an external view illustrating a schematic configuration of the endoscope apparatus.

FIGS. 1 and 2 are a diagram and a view illustrating a schematic configuration of an endoscope apparatus 10 according to an embodiment of the present invention. Note that, in the present specification, the endoscope is not limited to a medical endoscope (an esophagogastroduodenoscope, a colonoscope, an ultrasonic endoscope, a cystoscope, a pyeloscope, a bronchoscope, or the like) or an industrial endoscope, and refers to a general type of apparatus having an insertion section to be inserted into an observation object O.

In the following, a medical endoscope will be described as an example of the endoscope.

The endoscope apparatus 10 according to the present embodiment includes an endoscope 12, a main body (video processor) 14, an image display (monitor) 16, and an input device 18. An illuminator 20 configured to emit illumination light IL to the observation object O is provided for the endoscope 12 and the main body 14. Here, the observation object O is, for example, an affected portion or a disease portion in a subject (e.g., a body cavity (lumen)).

The endoscope 12 includes an imager 22 configured to detect reflected and scattered light RL of the illumination light IL radiated to the observation object O and output an imaging signal. The input device 18 is connected to the main body 14 or is arranged on the main body 14, and allows various user instructions such as specification of an emphasis mode to be detailed below to be input to the main body 14. The main body 14 includes an image processor 24 configured to generate a display image from the imaging signal of the imager 22 of the endoscope 12, and an emphasis mode setting unit 26 configured to set the illuminator 20 and the image processor 24 according to an emphasis mode input to the input device 18. The image display 16 is connected to the main body 14 and displays the display image formed by the image processor 24 as an observation object image.

In the endoscope 12, a thin and long insertion section 28, which is a bendable member, and a control section 30 coupled to a proximal end of the insertion section 28. The endoscope 12 is a tubular insertion apparatus having its tubular insertion section 28 to be inserted into the body cavity.

The insertion section 28 includes, from its distal end to its proximal end, a distal end hard section 32, a bendable section 34, and a flexible tube section 36. Here, a proximal end of the distal end hard section 32 is coupled to a distal end of the bendable section 34, and a proximal end of the bendable section 34 is coupled to a distal end of the flexible tube section 36.

The distal end hard section 32 is the distal end of the insertion section 28 and is also a distal end of the endoscope 12, and is a hard member. The imager 22 is provided in the distal end hard section 32.

The bendable section 34 can be bent in a desirable direction such as an up, down, right, or left direction, in accordance with an operation by a user (an operator such as a medical doctor) of a bend control section 38 provided in the control section 30. The user operates the bend control section 38 to bend the bendable section 34. The position and direction of the distal end hard section 32 are changed with the bend of the bendable section 34, and the observation object O is captured within the observation field of view of the imager 22. The illumination light IL is radiated from the illuminator 20 to the captured observation object O, and the observation object O is illuminated. The bendable section 34 is formed of coupling joint rings (not illustrated) along a longitudinal axis direction of the insertion section 28.

The flexible tube section 36 has desirable flexibility and can be bent by an external force. The flexible tube section 36 is a tubular member extending from a main body section 40 (described below) of the control section 30.

The control section 30 includes the main body section (scope) 40, a grip section 42, and a universal cord 44. The flexible tube section 36 extends from a distal end of the main body section 40. The grip section 42 is coupled to a proximal end of the main body section 40 and is to be held by the user who operates the endoscope 12. The universal cord 44 connects the grip section 42 and the main body 14.

In the grip section 42, the bend control section 38 for operating operation wires (not illustrated) is arranged to bend the bendable section 34. The bend control section 38 includes a right/left bend control knob that bends and controls the bendable section 34 rightward or leftward, an up/down bend control knob that bends and controls the bendable section 34 upward or downward, and a fixing knob that fixes the position of the bent bendable section 34.

A bend operation driving section (not shown) in a right and left direction, which is driven by the right/left bend control knob, is connected to the right/left bend control knob. A bend operation driving section (not shown) in an up and down direction, which is driven by the up/down bend control knob, is connected to the up/down bend control knob. The bend operation driving section in the up and down direction and the bend operation driving section in the right and left direction are disposed in the grip section 42, for example.

The bend operation driving section in the right and left direction is connected to a single right-and-left-direction operation wire (not illustrated) that is inserted through the control section 30, flexible tube section 36, and bendable section 34, and both ends of the right-and-left-direction operation wire are connected to the distal end of the bendable section 34.

Further, the bend operation driving section in the up and down direction is connected to a single up-and-down-direction operation wire (not illustrated) that is inserted through the control section 30, the flexible tube section 36, and the bendable section 34. The up-and-down-direction operation wire and the right-and-left-direction operation wire are different members and can be operated independently of each other. Both ends of the up-and-down-direction operation wire are connected to the distal end of the bendable section 34.

The right/left bend control knob bends the bendable section 34 in the right and left direction via the bend operation driving section in the right and left direction and the right-and-left-direction operation wire. Further, the up/down bend control knob bends the bendable section 34 in the up and down direction via the bend operation driving section in the up and down direction and the up-and-down-direction operation wire.

The bend control section 38 (the right/left bend control knob and the up/down bend control knob), the bend operation driving section in the right and left direction, the right-and-left-direction operation wire, the bend operation driving section in the up and down direction, and the up-and-down-direction operation wire constitute a bend control mechanism that controls the bendable section 34 to bend the bendable section 34.

Each of the sections and units will be described in more detail.

<Input Device 18>

The user can set an arbitrary emphasis mode to the endoscope apparatus 10 via the input device 18.

In the emphasis modes as seen from the surface of the observation object O, the degrees of emphasis of superficial blood vessels located near a surface, intermediate blood vessels located at a deeper position than the superficial blood vessels, and deep blood vessels located at a further deeper position than the intermediate blood vessels are respectively set. The user selects an arbitrary emphasis mode from among the plurality of preset emphasis modes according to the purpose of observation and inputs the selected emphasis mode through the input device 18.

For example, in the case of performing an observation focusing only on the superficial blood vessels, the user can input a "superficial blood vessel mode" by the input device 18. In the case of slightly suppressing the emphasis of the superficial blood vessels and the intermediate blood vessels in order to perform an observation focusing on the intermediate blood vessels and the deep blood vessels, the user can input a "superficial and intermediate blood vessel intermediate emphasis-deep blood vessel emphasis mode" by the input device 18. By selecting such a "superficial and intermediate blood vessel intermediate emphasis-deep blood vessel emphasis mode, the endoscope apparatus 10 can be set to obtain an image in which the degree of emphasis of the deep blood vessels is strong and the degrees of emphasis of the superficial blood vessels and the intermediate blood vessels are weak.

Note that the user can individually switch ON and OFF of highlight of the superficial blood vessels, the intermediate blood vessels, and the deep blood vessels, and can individually input the respective degrees of emphasis by the input device 18 regardless of the setting of such an emphasis mode.

Emphasis mode information input by the input device 18 is output to the emphasis mode setting unit 26.

<Illuminator 20>

The illuminator 20 includes laser light sources 46-1 to 46-6 (six laser light sources in the present embodiment), a light source driver 48, six optical fibers 50-1 to 50-6, a light combiner 52, an optical fiber 54, and a light converter 56. The laser light sources 46-1 to 46-6, the light source driver 48, the optical fibers 50-1 to 50-6, the light combiner 52, and part of the optical fiber 54 are arranged inside the main body 14, and the remaining part of the optical fiber 54 and the light converter 56 are arranged inside the endoscope 12.

Here, the laser light source 46-1 (laser 1) is a laser light source (a first emphasis narrowband light source) having a peak wavelength of 415 nm, and emits first laser light (first emphasis narrowband light).

The laser light source 46-2 (laser 2) is a laser light source (a first non-emphasis narrowband light source) having a peak wavelength of 445 nm, and emits second laser light (first non-emphasis narrowband light).

The laser light source 46-3 (laser 3) is a laser light source (a second emphasis narrowband light source) having a peak wavelength of 540 nm, and emits third laser light (second emphasis narrowband light).

The laser light source 46-4 (laser 4) is a laser light source (a second non-emphasis narrowband light source) having a peak wavelength of 515 nm, and emits fourth laser light (second non-emphasis narrowband light).

The laser light source 46-5 (laser 5) is a laser light source (a third emphasis narrowband light source) having a peak wavelength of 595 nm, and emits fifth laser light (third emphasis narrowband light).

Then, the laser light source 46-6 (laser 6) is a laser light source (a third non-emphasis narrowband light source) having a peak wavelength of 635 nm, and emits sixth laser light (third non-emphasis narrowband light).

The light source driver 48 controls driving of the plurality of laser light sources 46-1 to 46-6.

The optical fibers 50-1 to 50-6 guide the laser light emitted from the laser light sources 46-1 to 46-6 to the light combiner 52.

The light combiner 52 is, for example, an optical fiber combiner, which combines the laser light emitted from the laser light sources 46-1 to 46-6 and guided in the optical fibers 50-1 to 50-6.

The optical fiber 54 guides the laser light combined by the light combiner 52 to the light converter 56.

The light converter 56 is disposed in the distal end hard section 32 of the insertion section 28 in which the imager 22 is disposed. The light converter 56 converts optical characteristics of the laser light guided from the main body 14 by the optical fiber 54 inserted through the universal cord 44, the control section 30, and the insertion section 28 of the endoscope 12, and radiates the laser light to the observation object O as the illumination light IL.

A more specific configuration of each of the units and sections in the illuminator 20 is as follows.

<Laser Light Source 46-1 (Laser 1)>

Figure 3:
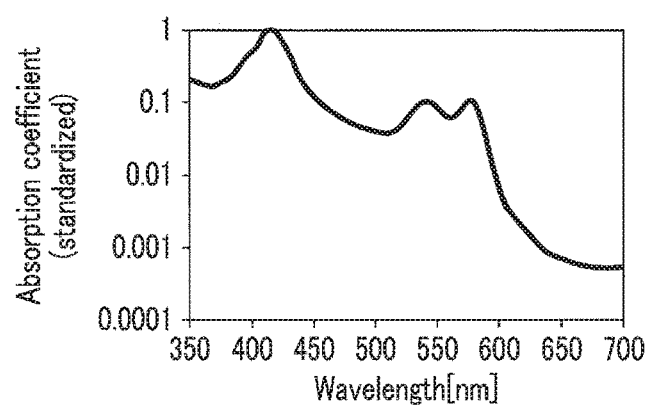
FIG. 3 is a diagram illustrating an optical absorption spectrum of oxyhemoglobin.

In the present embodiment, oxyhemoglobin contained in the blood in blood vessels is assumed to be the diagnosis target substance present in the observation object O. FIG. 3 illustrates an optical absorption spectrum of the oxyhemoglobin (hereinafter simply referred to as hemoglobin).

The laser light source 46-1 (laser 1) is a laser light source having the peak wavelength of 415 nm. The first laser light having the peak wavelength of 415 nm has a reach length up to a superficial region of the observation object O (the definition of the reach length will be mentioned below). Further, the peak wavelength 415 nm of the first laser light is a maximum wavelength that takes a maximum value in a blue range (the definition of a color range will be mentioned below) of the optical absorption spectrum of the hemoglobin that is the diagnosis target substance, and absorption in the hemoglobin contained in the blood in the blood vessels in the surface (hereinafter simply referred to as "superficial blood vessels") is large. Therefore, in the case of radiating the first laser light to the observation object O, a difference between light intensity in the superficial blood vessels to reflected and scattered light RL and light intensity in the vicinity of the superficial blood vessels to the reflected and scattered light RL is large. In other words, the contrast for the superficial blood vessels is high. That is, the superficial blood vessels are emphasized.

Therefore, the first laser light is referred to as emphasis narrowband light for the superficial blood vessels, and the laser light source 46-1 (laser 1) is referred to as an emphasis narrowband light source for the superficial blood vessels.

The peak wavelength of the first laser light is not limited to 415 nm. The peak wavelength of the first laser light may be another value as long as the peak wavelength or a central wavelength is included in the emphasis wavelength range for the superficial blood vessels.

Further, the emphasis wavelength range for the superficial blood vessels need not be a wavelength range including the maximum wavelength that takes a maximum value in the blue range of the optical absorption spectrum of the hemoglobin, and may be a wavelength range including a blue-region largest wavelength that takes a largest value in the blue range of the optical absorption spectrum of the hemoglobin.

Here, when the emphasis wavelength range for the superficial blood vessels is a wavelength range within ±20 nm for at least one of the maximum wavelength that takes the maximum value in the blue range of the absorption spectrum of the hemoglobin and the blue-region largest wavelength that takes the largest value in the blue range, the light absorption is large and the superficial blood vessels are emphasized, and thus it is favorable. Further, when the emphasis wavelength range for the superficial blood vessels is a wavelength range within ±10 nm, the light absorption is larger and the superficial blood vessels are further emphasized, and thus it is favorable.

Further, when the emphasis wavelength range for the superficial blood vessels is a wavelength range that has a value equal to or more than ½ of the maximum value in the blue range of the absorption spectrum of the hemoglobin or the largest value in the blue range, the absorption is large, and thus it is favorable.

In the blue range of the optical absorption spectrum of the hemoglobin, the maximum wavelength and the blue-region largest wavelength are the same.

<Laser Light Source 46-2 (Laser 2)>

The laser light source 46-2 (laser 2) is a laser light source having the peak wavelength of 445 nm. The second laser light having the peak wavelength of 445 nm has a reach length up to the superficial region of the observation object O, similarly to the first laser. However, the peak wavelength 445 nm of the second laser light is included in a non-emphasis wavelength range for the superficial blood vessels, which does not include the above-described emphasis wavelength range for the superficial blood vessels. In the case of radiating the second laser light to the observation object O, a difference between the light intensity in the superficial blood vessels to the reflected and scattered light RL and the light intensity in the vicinity of the superficial blood vessels to the reflected and scattered light RL is small. In other words, the contrast for the superficial blood vessels is low. That is, the superficial blood vessels are not emphasized.

Therefore, the second laser light is referred to as non-emphasis narrowband light for the superficial blood vessels, and the laser light source 46-2 (laser 2) is referred to as a non-emphasis narrowband light source for the superficial blood vessels.

The peak wavelength of the second laser light is not limited to 455 nm. The peak wavelength of the second laser light may be another value as long as the value is included in the non-emphasis wavelength range in which the superficial blood vessels are not highlighted.

The non-emphasis wavelength range for the superficial blood vessels is a range that does not include the emphasis wavelength range for the superficial blood vessels.

The non-emphasis wavelength range for the superficial blood vessels is favorably a range that includes at least one of a minimum wavelength that takes a minimum value in the blue range of the optical absorption spectrum of the hemoglobin and a blue-region smallest wavelength that takes a smallest value in the blue range of the optical absorption spectrum of the hemoglobin.

Here, when the non-emphasis wavelength range for the superficial blood vessels is a wavelength range within ±20 nm of at least one of the above-mentioned minimum wavelength and the above-mentioned smallest wavelength, the light absorption is small and the superficial blood vessels are not emphasized, and thus it is favorable. Further, when the non-emphasis wavelength range is a wavelength range within ±10 nm, the light absorption is smaller and the superficial blood vessels are further suppressed, and thus it is favorable.

Further, when the non-emphasis wavelength range for the superficial blood vessels is a wavelength range that has a value equal to or less than 1.5 times of at least one of the above-mentioned minimum value and the above-mentioned smallest value in the blue range, the absorption is small, and thus it is favorable.

Further, when the non-emphasis wavelength range for the superficial blood vessels is a wavelength range that has a value equal to or less than ½ of at least one of the maximum value in the blue range and the largest value in the blue range, the absorption is small, and thus it is favorable.

<Laser Light Source 46-3 (Laser 3)>

The laser light source 46-3 (laser 3) is a laser light source having a peak wavelength of 540 nm. The third laser light having the peak wavelength of 540 nm has a reach length up to the intermediate region of the observation object O, which is deeper than the superficial region. Further, the peak wavelength 540 nm of the third laser light is a maximum wavelength that takes a maximum value in the green range of the optical absorption spectrum of the hemoglobin, and the absorption in the intermediate blood vessels is large. Therefore, in the case where the third laser light is radiated to the observation object O, the difference between the light intensity in the intermediate blood vessel to the reflected and scattered light RL and the light intensity in the vicinity of the intermediate blood vessels to the reflected and scattered light RL is large. In other words, the contrast for the intermediate blood vessels is high. That is, the intermediate blood vessels are emphasized.

Therefore, the third laser light is referred to as emphasis narrowband light for the intermediate blood vessels, and the laser light source 46-3 (laser 3) is referred to as an emphasis narrowband light source for the intermediate blood vessels.

The peak wavelength of the third laser light is not limited to 540 nm. The peak wavelength of the third laser light may be another value as long as the peak wavelength or central wavelength is included in the emphasis wavelength range corresponding to the intermediate blood vessels.

Further, the emphasis wavelength range for the intermediate blood vessels need not be the wavelength range including the maximum wavelength that takes a maximum value in the green range of the optical absorption spectrum of the hemoglobin, and may be a wavelength range including a green-region largest wavelength that takes a largest value in the green range of the optical absorption spectrum of the hemoglobin.

Here, when the emphasis wavelength range for the intermediate blood vessels is a wavelength range within ±20 nm for at least one of the maximum wavelength that takes a maximum value in the green range of the optical absorption spectrum of the hemoglobin and the green-region largest wavelength that takes a largest value in the green range, the light absorption is large and the intermediate blood vessels are emphasized, and thus it is favorable. Further, when the emphasis wavelength range is a wavelength range within ±10 nm, the light absorption is larger and the intermediate blood vessels are further emphasized, and thus it is favorable.

Further, when the emphasis wavelength range for the intermediate blood vessels is a wavelength range that has a value equal to or more than ½ of the maximum value in the green range of the absorption spectrum of the hemoglobin or the largest value in the green range, the absorption is large, and thus it is favorable.

<Laser Light Source 46-4 (Laser 4)>

The laser light source 46-4 (laser 4) is a laser light source having a peak wavelength of 515 nm. The fourth laser light having the peak wavelength of 515 nm has a reach length up to the intermediate region of the observation object O, similarity to the third laser light. However, the peak wavelength 515 nm of the fourth laser light is included in the non-emphasis wavelength range for the intermediate blood vessels, which does not include the above-mentioned emphasis wavelength range for the intermediate blood vessels. In the case of radiating the fourth laser light to the observation object O, a difference between the light intensity in the intermediate blood vessels to the reflected and scattered light RL and the light intensity in the vicinity of the intermediate blood vessels to the reflected and scattered light RL is small. In other words, the contrast for the intermediate blood vessels is low. That is, the intermediate blood vessels are not emphasized.

Therefore, the fourth laser light is referred to as non-emphasis narrowband light for the intermediate blood vessels, and the laser light source 46-4 (laser 4) is referred to as a non-emphasis narrowband light source for the intermediate blood vessels.

The peak wavelength of the fourth laser light is not limited to 515 nm. The peak wavelength of the fourth laser light may be another value as long as it is included in the non-emphasis wavelength range in which the intermediate blood vessels are not highlighted.

The non-emphasis wavelength range for the intermediate blood vessels is a range that does not include the emphasis wavelength range for the intermediate blood vessels.

Further, the non-emphasis wavelength range for the intermediate blood vessels is favorably a range that includes at least one of a minimum wavelength that takes a minimum value in the green range of the optical absorption spectrum of the hemoglobin and a green-region smallest wavelength that takes a smallest value in the green range of the optical absorption spectrum of the hemoglobin.

Here, when the non-emphasis wavelength range for the intermediate blood vessels is a wavelength range within ±20 nm of at least one of the above-mentioned minimum wavelength and the above-mentioned smallest wavelength, the light absorption is small and the intermediate blood vessels are not emphasized, and thus it is favorable. Further, when the non-emphasis wavelength range is a wavelength range within ±10 nm, the light absorption is smaller and the intermediate blood vessels are further suppressed, and thus it is favorable.

Further, when the non-emphasis wavelength range for the intermediate blood vessels is a wavelength range that has a value equal to or less than 1.5 times of at least one of the above-mentioned minimum value and the above-mentioned smallest value in the green range, the light absorption is small, and thus it is favorable.

Alternatively, when the non-emphasis wavelength range for the intermediate blood vessels is a wavelength range that has a value equal to or less than ½ of at least one of the maximum value in the green range and the largest value in the green range, the absorption is small, and thus it is favorable.

<Laser Light Source 46-5 (Laser 5)>

The laser light source 46-5 (laser 5) is a laser light source having a peak wavelength of 595 nm. The fifth laser light having the peak wavelength of 595 nm has a reach length up to a deep region of the observation object O, which is deeper than the intermediate region. The peak wavelength 595 nm of the fifth laser light is included in the emphasis wavelength range for the deep blood vessels, which is a wavelength range within ±20 nm of the red-region largest wavelength 590 nm that takes a largest value in the red range of the optical absorption spectrum of the hemoglobin, and is a wavelength range that has a value equal to or more than ½ of the red-region largest value, and the absorption in the deep blood vessels is large. Therefore, in the case of radiating the fifth laser light to the observation object O, a difference between light intensity in the deep blood vessels to the reflected and scattered light RL and light intensity in the vicinity of the deep blood vessels to the reflected and scattered light RL is large. In other words, the contrast for the deep blood vessels is high. That is, the deep blood vessels are emphasized.

Therefore, the fifth laser light is referred to as emphasis narrowband light for the deep blood vessels, and the laser light source 46-5 (laser 5) is referred to as an emphasis narrowband light source for the deep blood vessels.

The peak wavelength of the fifth laser light is not limited to 595 nm. The peak wavelength of the fifth laser light may be another value as long as the peak wavelength or central wavelength is included in the emphasis wavelength range corresponding to the deep blood vessels.

Further, the emphasis wavelength range for the deep blood vessels need not be the wavelength range including the maximum wavelength that takes a maximum value in the red range of the optical absorption spectrum of the hemoglobin, and may be a wavelength range including a red-region largest wavelength that takes a largest value in the red range of the optical absorption spectrum of the hemoglobin.

Here, when the emphasis wavelength range corresponding to the deep blood vessels is a wavelength range within ±20 nm of at least one of the maximum wavelength that takes a maximum value in the red range of the optical absorption spectrum of the hemoglobin and the red-region largest wavelength that takes a largest value in the red range, the light absorption is large and the deep blood vessels are emphasized, and thus it is favorable. Further, when the emphasis wavelength range is a wavelength range within ±10 nm, the light absorption is larger and the deep blood vessels are further emphasized, and thus it is favorable.

Further, when the emphasis wavelength range for the deep blood vessels is a wavelength range that has a value equal to or more than ½ of the maximum value in the red range of the absorption spectrum of the hemoglobin or the largest value in the red range, the absorption is large, and thus it is favorable.

<Laser Light Source 46-6 (Laser 6)>

The laser light source 46-6 (laser 6) is a laser light source having a peak wavelength of 635 nm. The sixth laser light having the peak wavelength of 635 nm has a reach length up to the deep region of the observation object O, similarly to the fifth laser light. However, the peak wavelength 635 nm of the sixth laser light is included in the non-emphasis wavelength range for the deep blood vessels, which does not include the above-mentioned emphasis wavelength range for the deep blood vessels. In the case of radiating the sixth laser light to the observation object O, a difference between the light intensity in the deep blood vessels to the reflected and scattered light RL and the light intensity in the vicinity of the deep blood vessels to the reflected and scattered light RL is small. In other words, the contrast for the deep blood vessels is low That is, the deep blood vessels are not emphasized.

Therefore, the sixth laser light is referred to as non-emphasis narrowband light for the deep blood vessels, and the laser light source 46-6 (laser 6) is referred to as a non-emphasis narrowband light source for the deep blood vessels.

The peak wavelength of the sixth laser light is not limited to 635 nm. The peak wavelength of the sixth laser light may be another value as long as it is included in the non-emphasis wavelength range in which the deep blood vessels are not highlighted.

The non-emphasis wavelength range for the deep blood vessels is a range that does not include the emphasis wavelength range for the deep blood vessels.

Further, the non-emphasis wavelength range for the deep blood vessels is favorably a range that includes at least one of a minimum wavelength that takes a minimum value in the red range of the optical absorption spectrum of the hemoglobin and a red-region smallest wavelength that takes a smallest value in the red range of the optical absorption spectrum of the hemoglobin.

Here, when the non-emphasis wavelength range corresponding to the deep blood vessels is a wavelength range within ±20 nm of at least one of the above-mentioned minimum wavelength and the above-mentioned smallest wavelength, the light absorption is small and the deep blood vessels are not emphasized, and thus it is favorable. Further, when the non-emphasis wavelength range is a wavelength range within ±10 nm, the light absorption is smaller and the deep blood vessels are suppressed, and thus it is favorable.

Further, when the non-emphasis wavelength range for the deep blood vessels is a wavelength range that has a value equal to or less than 1.5 times of at least one of the above-mentioned minimum value and the above-mentioned smallest value in the red range, the light absorption is small, and thus it is favorable.

Alternatively, when the non-emphasis wavelength range for the deep blood vessels is a wavelength range that has a value equal to or less than ½ of at least one of the maximum value in the red range and the largest value in the red range, the absorption is small, and thus it is favorable.

Note that the narrowband light, that is, the emphasis narrowband light and the non-emphasis narrowband light may be light other than the laser light. The narrowband light is favorably narrowband light having a wavelength width of 50 nm or less, and more favorably narrowband light having a wavelength width of 5 nm or less. The wavelength width is, for example, a wavelength width defined by the full width at half maximum (FWHM) or the root mean square (RMS). The wavelength width of half-value-width laser light is, for example, 1 nm. A light source may be, for example, an LED, a light source using fluorescent light exited by LED light or laser light, or a broadband light source that generates narrowband light using spectral filters. In the configuration to generate the narrowband light using spectral filters, wavelengths of narrowband light to be emitted are switched by mechanically switching the spectral filters.

<Color Range>

The blue range, green range, and red range described above are defined by the following wavelength ranges:

Blue range: 400 to 510 nm,
Green range: 490 to 610 nm,
Red range: 590 to 700 nm.

These wavelength ranges are wavelength ranges obtained by equally dividing a wavelength range from 400 to 700 nm of the visible light range into three ranges and providing an overlap of 20 nm to between the adjacent ranges. When the wavelengths are set based on these well-balanced wavelength ranges, the illumination light IL having good color reproducibility can be generated in the case where wavelengths are included in the respective color ranges of the blue range, green range, and red range.

For example, a wavelength range that is less than 400 nm and a wavelength range that is 700 nm or more may be allocated to the blue range and the red range, respectively. In this case, the blue range, green range, and red range are defined by the following wavelength ranges:

Blue range: 380 to 510 nm,
Green range: 490 to 610 nm,
Red range: 590 to 780 nm.

Figure 4:
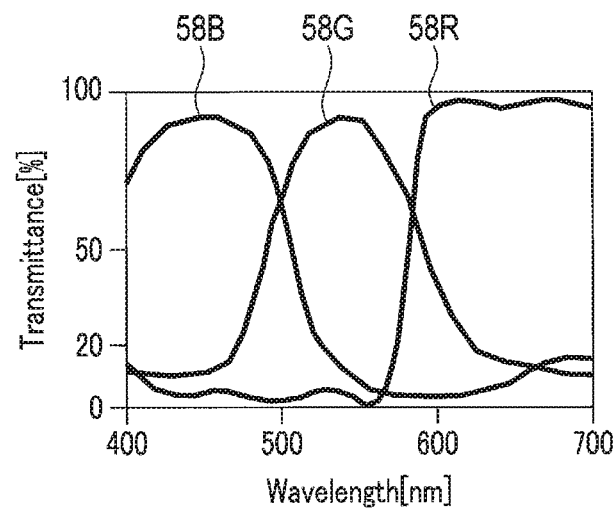
FIG. 4 is a diagram illustrating an example of spectroscopic characteristics of color filters in an imager.

For example, when the imager 22 acquires a spectral image, using the color filters, the blue range, green range, and red range may be defined using the spectroscopic characteristics of the color filters. FIG. 4 illustrates an example of the spectroscopic characteristics 58B of the blue (B) color filter, the spectroscopic characteristics 58G of the green (G) color filter, and the spectroscopic characteristics 58R of the red (R) color filter. Here, for example, a wavelength range having the transmittance of 20% or more is defined as each color range in each color filter. That is, as illustrated in FIG. 4, the blue range is 400 to 525 nm, the green range is 470 to 625 nm, and the red range is 570 to 700 nm.

As illustrated in FIG. 4, there are very few wavelength ranges in which the transmittance of the color filters is zero, and the transmittance is several % to 10% in a broad range of the visible light. The transmittance of several % to 10% can be regarded as a negligible level in capturing a color image, so that color ranges should be favorably defined based on the range in which the transmittance is 20% or higher.

<Maximum Value and Color-Range Largest Value in Each Color Range>

Figure 5:
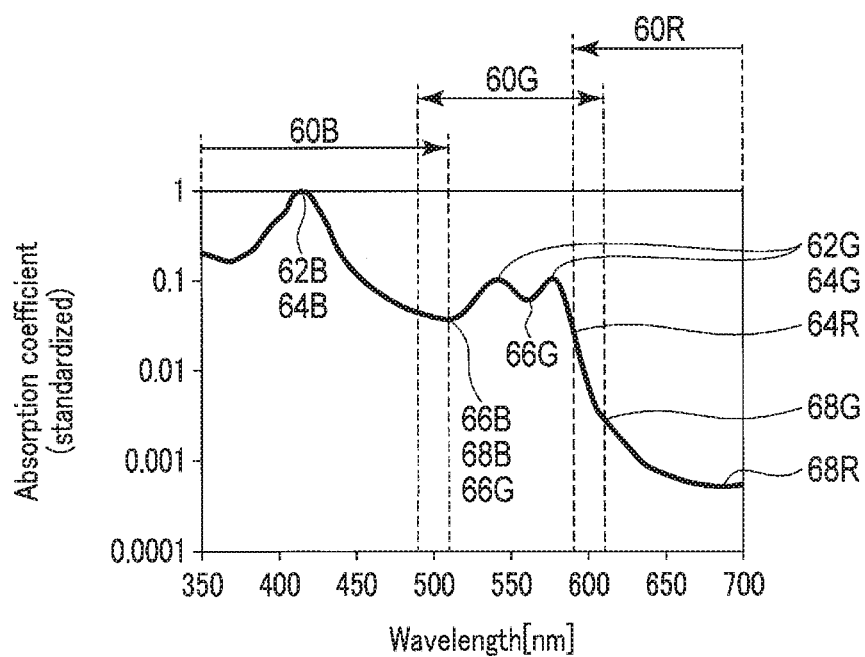
FIG. 5 is a diagram for describing a maximum value and a color-range largest value in each color range.

The maximum value and the color-range largest value in each color range of oxyhemoglobin with respect to the absorption spectrum are illustrated in FIG. 5.

That is, in the blue range 60B, the maximum wavelength that takes the blue-region maximum value 62B and the color-range largest wavelength that takes the blue-region largest value 64B are the same wavelength of 415 nm, and the minimum wavelength that takes the blue-region minimum value 66B and the color-range smallest wavelength that takes the blue-region smallest value 68B are the same wavelength of 500 nm.

In contrast, in the green range 60G, the maximum wavelength that takes the green-region maximum value 62G and the color-range largest wavelength that takes the green-region largest value 64G are the same wavelength, but there are two wavelengths of 540 nm and about 575 nm. The number of the minimum wavelengths that take the green-region minimum value 66G is also two. One is the wavelength of 500 nm and the other is the wavelength of 560 nm. The color-range smallest wavelength that takes the green-region smallest value 68G is the wavelength of 610 nm.

Then, in the red range 60R, neither a maximum value nor a minimum value exists, and the color-range largest wavelength that takes the red-region largest value 64R is the wavelength of 590 nm and the color-range smallest wavelength that takes the red-region smallest value 68R is the wavelength of 685 nm.

<Reach Length>

In the case where light of a wavelength range from near ultraviolet to near infrared is radiated to a living body (observation object O), light having a longer wavelength has a deeper reach length into the living body, due to light scattering properties and light absorption properties in living tissues (an epithelial tissue, a mucous membrane, a body fluid, or the like).

Figure 6A:
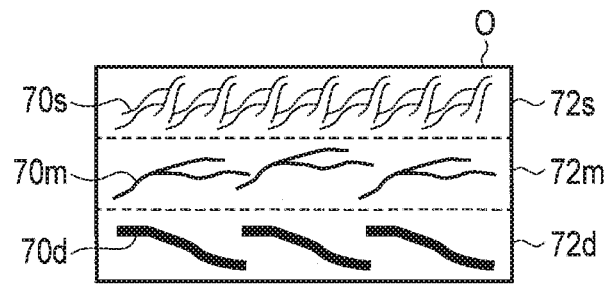
FIG. 6A is a diagram schematically illustrating a laminated configuration of blood vessels.

For example, as illustrated in FIG. 6A, the blood vessels of a living body (observation object O) include superficial blood vessels (capillaries) 70s located near the surface of the living body, intermediate blood vessels (blood vessels thicker than the capillaries) 70m located in deeper portions, and deep blood vessels (blood vessels thicker than the intermediate blood vessels) 70d located in further deeper portions. Here, the region where the superficial blood vessels 70s exist is referred to as a superficial region 72s of the living body, the region where the intermediate blood vessels 70m exist is referred to as an intermediate region 72m, and the region where the deep blood vessels 70d exist is referred to as a deep region 72d.

Figure 6B:
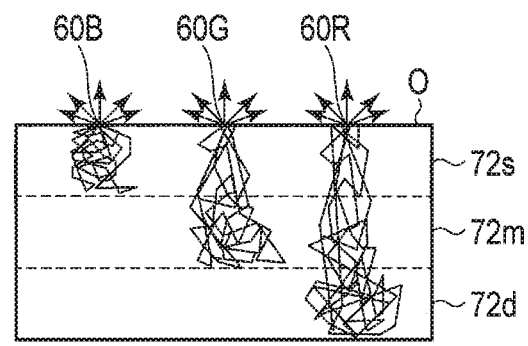
FIG. 6B is a diagram schematically illustrating a reach length of light in each color range.

As illustrated in FIG. 6B, in the case where light of the blue range 60B on the short wavelength side is radiated to the living body (observation object O), the light of the blue range 60B has a reach length up to the superficial region 72s of the living body, and is greatly influenced by the absorption by the superficial blood vessels 70s and is reflected in an image of the living body (observation object O). Further, in the case where light of the green range 60G is radiated, the light of the green range 60G has a reach length up to the intermediate region 72m of the living body, and is greatly influenced by the absorption by the intermediate blood vessels 70m and is reflected in an image of the living body (observation object O). Further, in the case where light of the red range 60R is radiated, the light of the red range 60R has a reach length up to the deep region 72d of the living body, and is greatly influenced by the absorption by the deep blood vessels 70d and is reflected in an image of the living body (observation object O).

For example, the reach length is defined as follows:

Light intensity $I(x)$ at a distance x within the living body (observation object O) is expressed by $I(x)=I_0 \exp[-\alpha x]$, where incident light intensity is $I_0$ and an attenuation coefficient is $\alpha$.

Here, the reach length is defined as the reciprocal of attenuation coefficient $\alpha$, i.e., a distance at which the light intensity becomes $1/e$. Note that the attenuation coefficient $\alpha$ is defined by Equation (1) set forth below, where an absorption coefficient is $\mu_a$, a scattering coefficient is $\mu_s$, an anisotropy factor is g, and an equivalent scattering coefficient is given by $\mu_s'=(1-g)\mu_s$.

$$\alpha = \sqrt{(3\mu_a(\mu_a+\mu_s'))} \quad (1)$$

Further, for example, the absorption coefficient $\mu_a$, the scattering coefficient $\mu_s$, and the equivalent scattering coefficient $\mu_s'$ may be simply used as the attenuation coefficient $\alpha$.

The absorption coefficient $\mu_a$, the scattering coefficient $\mu_s$, and the anisotropy factor g differ depending upon the living body (observation object O) and the wavelength.

<Optical Fibers 50-1 to 50-6 and 54>

The optical fibers 50-1 to 50-6 and the optical fiber 54 are single-wire fibers having a core diameter of several tens of μm to several hundreds of μm, for example. A coupling lens (not illustrated) for converging the laser light emitted from the laser source and coupling the laser light to the optical fiber is disposed between each of the laser light sources 46-1 to 46-6 and each of the optical fibers 50-1 to 50-6.

Note that a bundle fiber made of a bundle of optical fibers may be used in place of the optical fiber 54.

<Light Source Driver 48>

The light source driver 48 can control ON/OFF, a driving current, and a driving method (continuous driving (CW), pulse driving, or the like) of the laser light sources 46-1 to 46-6 independently of one another.

The light source driver 48 can control a combination of the lasers to be turned on, a light quantity ratio, and light emission timing of the laser light sources 46-1 to 46-6 according to the emphasis mode information from the input device 18.

Note that the light source driver 48 may be configured by a hardware circuit or by a processor. In the case of configuring the light source driver 48 by a processor, a program code for causing the processor to function as the light source driver 48 by being executed by the processor is stored in an external memory (not illustrated) accessible by the processor.

<Light Converter 56>

Figure 7:
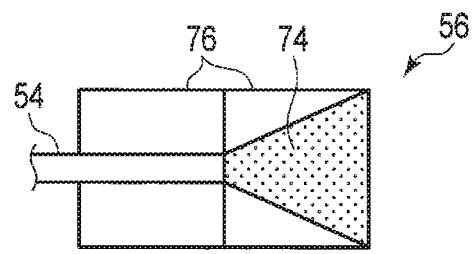
FIG. 7 is a schematic view illustrating a light converter.

As illustrated in FIG. 7, the light converter 56 is made by disposing a diffusing member 74 formed of alumina particles or the like at the distal end of the optical fiber 54. The distal end of the optical fiber 54 and the diffusing member 74 are held by a holder 76, and the positional relationship between them is defined.

The diffusing member 74 has a function to diffuse rays of laser light guided by the optical fiber 54 and to change the laser lights to have desirable light distribution. The diffusing member 74 does not convert the wavelength of the light.

Note that the light converter 56 may employ a lens or a combination of the lens and the diffusing member 74 in place of the diffusing member 74.

Further, in the case of using a bundle fiber in place of the optical fiber 54, the light converter 56 may employ a lens in place of the diffusing member 74.

<Imager 22>

The imager 22 detects the reflected and scattered light RL from the observation object O to generate an imaging signal. The imaging signal is output to the image processor 24 of the main body 14 as a primary image signal.

The imager 22 is, for example, a monochrome imager without color filters and sequentially receives, at different timings, the reflected and scattered light RL for rays of laser light sequentially emitted at different timings to generate an imaging signal.

The imager 22 may be a CCD imager or a CMOS imager.

Further, the imager 22 can be a color imager having three types of light detection elements including an R light detection element for detecting the red range 60R, a G light detection element for detecting the green range 60G, and a B light detection element for detecting the blue range 60B by color filters. An example of the spectroscopic characteristics of the color filters in the R light detection element, the G light detection element, and the B light detection element in this case is illustrated in FIG. 4.

The imager 22 as such a color imager generates an R imaging signal, a G imaging signal, and a B imaging signal for the three wavelength ranges of the red range 60R, the green range 60G, and the blue range 60B, separately and independently of one another, by means of the R light detection element, the G light detection element, and B light detection element.

<Emphasis Mode Setting Unit 26>

The emphasis mode setting unit 26 includes an emphasis mode storage 78, a light source setting unit 80, and an image setting unit 82.

The emphasis mode storage 78 includes a semiconductor memory in which light source drive information and image processing information. The light source drive information includes information of a light emission combination, a light emission pattern, and a light quantity ratio of the laser light sources 46-1 to 46-6 in the illuminator 20 in each emphasis mode. The image processing information includes information of a combination of image synthesis, a synthesis method, and a synthesis ratio in the image processor 24. The emphasis mode storage 78 outputs the light source drive information corresponding to the emphasis mode information from the input device 18 to the light source setting unit 80, and outputs the image processing information corresponding to the emphasis mode information from the input device 18 to the image setting unit 82.

The light source setting unit 80 outputs light source output pattern information indicating the light emission combination, the light emission pattern, and the light quantity ratio of the laser light sources 46-1 to 46-6 to the light source driver 48 of the illuminator 20 according to the light source drive information from the emphasis mode storage 78. The light source driver 48 controls the lighting of the laser light sources 46-1 to 46-6 according to the light source output pattern information. Note that the emphasis mode information from the input device 18 can be input to the light source setting unit 80, and the light source setting unit 80 can read the light source drive information from the emphasis mode storage 78 according to the emphasis mode information and set the light source output pattern information.

Here, in the case where the imager 22 is a monochrome imager, the imager 22 sequentially receives, at different timings, the reflected and scattered light RL for rays of laser light sequentially emitted at different timings to generate an imaging signal. The light emission combination and the light emission pattern in the light source output pattern information is information indicating when to turn on which of the laser light sources 46-1 to 46-6.

The image setting unit 82 outputs control information indicating the combination, the synthesis method, and the synthesis ratio of images to be synthesized in the image processor 24 to the image processor 24 according to the image processing information from the emphasis mode storage 78. The image processor 24 performs image processing for a video signal from the imager 22 according to the control information. Note that the emphasis mode information from the input device 18 can be input to the image setting unit 82, and the image setting unit 82 can read the combination, the synthesis method, and the synthesis ratio of synthesis images from the emphasis mode storage 78 according to the emphasis mode information, and set the control information.

The emphasis mode setting unit 26 (one or both of the light source setting unit 80 and the image setting unit 82) may be configured by a hardware circuit or by a processor. In the case of configuring the emphasis mode setting unit 26 by a processor, a program code for causing the processor to function as the emphasis mode setting unit 26 (the light source setting unit 80 and/or the image setting unit 82) by being executed by the processor is stored in an external memory (not illustrated) accessible by the processor.

<Image Processor 24>

The image processor 24 includes a primary image memory 84, an image selector 86, and an intermediate emphasis image generator 88. The intermediate emphasis image generator 88 includes a primary intermediate emphasis image generator 90 and a display image generator 92.

The primary image memory 84 includes a semiconductor memory configured to store a primary image signal that is an imaging signal acquired by the imager 22. The primary image memory 84 can store primary image signals corresponding to at least one cycle of the laser light emission pattern.

The image selector 86 selects primary image signals to be used for synthesis from among the primary image signals stored in the primary image memory 84 according to the control information from the image setting unit 82. The primary image memory 84 outputs the selected primary image signals to the primary intermediate emphasis image generator 90 and the display image generator 92 of the intermediate emphasis image generator 88.

The primary intermediate emphasis image generator 90 synthesizes part of the selected plurality of primary image signals, for example, two primary image signals, to generate a primary intermediate emphasis image signal in which the degree of emphasis of the blood vessels in a certain layer is adjusted. Note that the primary intermediate emphasis image generator 90 can read primary image signals to be used for generation of the primary intermediate emphasis image signal from the primary image memory 84 according to selection by the image selector 86, and generate the primary intermediate emphasis image signal.

The display image generator 92 combines the generated primary intermediate emphasis image signal and a selected remaining primary image signal and performs appropriate image correction to generate an intermediate emphasis image as a display image. Note that the display image generator 92 can read primary image signals to be used for generation of the intermediate emphasis image from the primary image memory 84 according to selection by the image selector 86, and generate the intermediate emphasis image signal.

The image synthesis method and the synthesis ratio in the primary intermediate emphasis image generator 90 and the display image generator 92 depend on the control information of the image setting unit 82. As the image correction in the display image generator 92, color correction and known emphasis processing such as edge emphasis processing can be used, for example.

Note that the image processor 24 (at least one of the primary image memory 84, the image selector 86, and the intermediate emphasis image generator 88 (the primary intermediate emphasis image generator 90 and the display image generator 92)) may be configured by a hardware circuit or by a processor. In the case of configuring the image processor 24 by a processor, a program code for causing the processor to function as the image processor 24 (at least one of the primary image memory 84, the image selector 86, and the intermediate emphasis image generator 88 (the primary intermediate emphasis image generator 90 and the display image generator 92)) by being executed by the processor is stored in an external memory (not illustrated) accessible by the processor.

<Image Display 16>

The image display 16 displays a display image generated by the image processor 24 as an observation object image. The image display 16 is a monitor such as a liquid crystal display.

Figure 8:
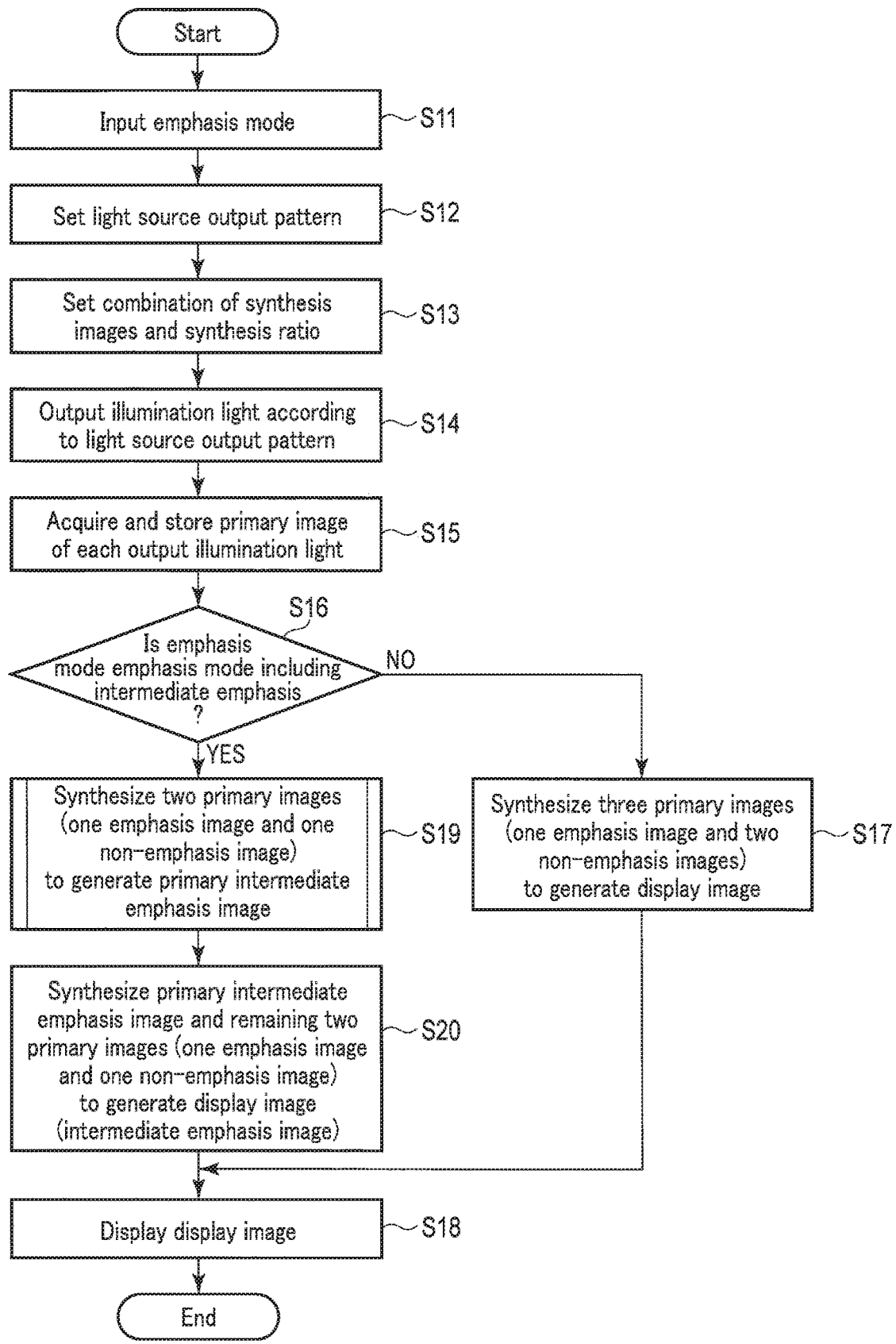
FIG. 8 is a flowchart for describing an operation of the endoscope apparatus.

Hereinafter, the operation of the endoscope apparatus 10 having the above-described configuration will be described with reference to the flowchart in FIG. 8.

As described above, when the user inputs the emphasis mode by the input device 18, the emphasis mode information indicating the emphasis mode is input to the emphasis mode setting unit 26 (step S11).

The light source setting unit 80 of the emphasis mode setting unit 26 sets one piece of light source output pattern information to be used from among a plurality of pieces of light source output pattern information stored in the emphasis mode storage 78 according to the input emphasis mode information, and outputs the light source output pattern information to the light source driver 48 of the illuminator 20 (step S12).

Further, the image setting unit 82 of the emphasis mode setting unit 26 sets one combination of synthesis images, one synthesis method, and one synthesis ratio from among a plurality of combinations of synthesis images, a plurality of synthesis methods, and a plurality of synthesis ratios stored in the emphasis mode storage 78 according to the input emphasis mode information, and outputs the set information to the image selector 86 of the image processor 24 as the control information (step S13).

The light source driver 48 of the illuminator 20 controls the combination of the lasers to be turned on, and the lighting times and light quantities of the laser light sources, for the laser light sources 46-1 to 46-6, according to the light source output pattern information set in the step S12, whereby rays of illumination light IL according to the emphasis mode input in step S11 is sequentially output from the light converter 56 (step S14). That is, selected laser light sources, of the laser light sources 46-1 to 46-6, are turned on one at a time in a time-divided fixed radiation cycle, and the rays of illumination light IL is sequentially emitted in the one radiation cycle.

The imager 22 detects the reflected and scattered light RL of each illumination light IL from the observation object O and acquires the primary image signal in one radiation cycle, and stores the primary image of each output illumination light to the primary image memory 84 of the image processor 24 (step S15).

The image selector 86 of the image processor 24 determines whether the emphasis mode input in step S11 is an emphasis mode including intermediate emphasis according to the control information set in step S13, and selects primary image signals to be used for synthesis from among the primary image signals stored in the primary image memory 84 (step S16).

In the case where the image selector 86 determines that the emphasis mode is not the emphasis mode including intermediate emphasis, the image selector 86 selects three primary image signals of one emphasis image signal and two non-emphasis image signals as the primary image signals to be used for synthesis Then, the display image generator 92 synthesizes the selected three primary image signals stored in the primary image memory 84 by the synthesis method and the synthesis ratio indicated by the control information set in step S13 to generate a display image (step S17).

The image display 16 displays the display image as an observation object image (step S18).

Here, the superficial blood vessel emphasis mode will be described as an example of the case where the emphasis mode is not the emphasis mode including intermediate emphasis, that is, the emphasis mode is an emphasis mode not including intermediate emphasis.

<Superficial Blood Vessel Emphasis Mode>

For example, in endoscopic examination, the superficial blood vessel emphasis mode is used when performing an observation focusing only on the blood vessels in the surface to diagnose a portion of what looks like lesions.

When the superficial blood vessel emphasis mode is input to the input device 18 by the user as the emphasis mode, the light source output pattern information and the control information according to the superficial blood vessel emphasis mode are output from the emphasis mode setting unit 26 to the light source driver 48 of the illuminator 20 and the image selector 86 of the image processor 24.

When the light source driver 48 receives the light source output pattern information according to the superficial blood vessel emphasis mode, the light source driver 48 repeatedly turns on the laser light source 46-1 (laser 1), the laser light source 46-4 (laser 4), and the laser light source 46-6 (laser 6) in that order as one cycle of radiation to cause the laser light sources 46-1, 46-4, and 46-6 to emit the first laser light, the fourth laser light, and the sixth laser light in order, as illustrated in FIG. 9. That is, one frame period that is a typical acquisition period of an imaging signal is divided into three subframe periods, as illustrated in FIG. 9, one laser light source is turned on in each subframe, and the laser light source to be turned on is sequentially switched in each subframe.

Figure 10:
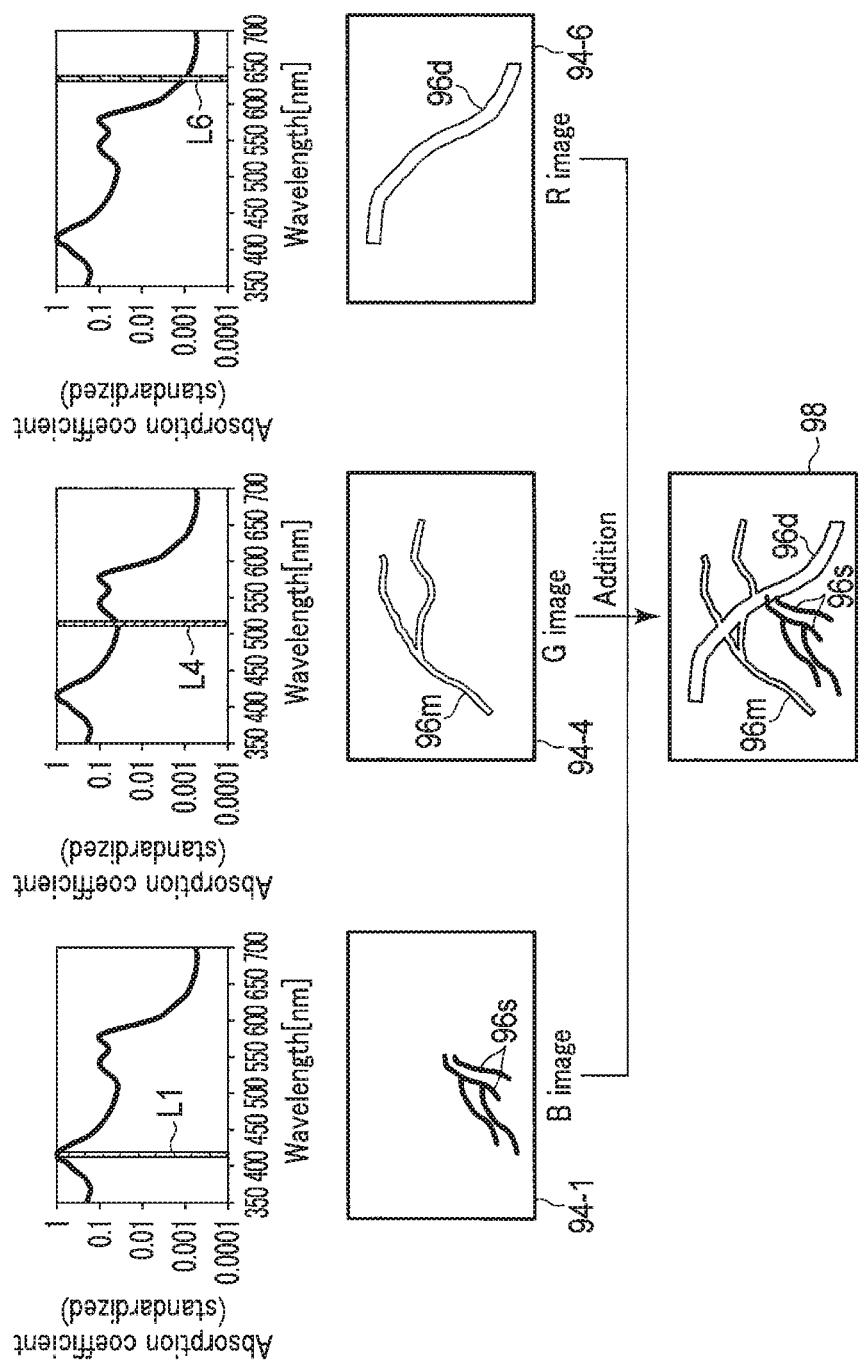
FIG. 10 is a diagram schematically illustrating a flow of display image generation in the superficial blood vessel emphasis mode.

Here, the laser light source 46-1 (laser 1) is the emphasis narrowband light source for the superficial blood vessels 70s (superficial region 72s), and the first laser light emitted from laser light source 46-1 (laser 1) is the emphasis narrowband light for the superficial blood vessels 70s (superficial region 72s). As illustrated in FIGS. 9 and 10, the wavelength of the first laser light (L1) that is the emphasis narrowband light for the superficial blood vessels 70s is 415 nm and is included in the blue range 60B. Note that, in FIG. 10, the vertical axis of the laser light spectrum is drawn in an arbitrary scale.

Further, the laser light source 46-4 (laser 4) is the non-emphasis narrowband light source for the intermediate blood vessels 70m (intermediate region 72m), and the fourth laser light emitted from laser light source 46-4 (laser 4) is the non-emphasis narrowband light for the intermediate blood vessels 70m (intermediate region 72m). As illustrated in FIGS. 9 and 10, the wavelength of the fourth laser light (L4) that is the non-emphasis narrowband light for the intermediate blood vessels 70m is 515 nm and is included in the green range 60G.

Then, the laser light source 46-6 (laser 6) is the non-emphasis narrowband light source for the deep blood vessels 70d (deep region 72d), and the sixth laser light emitted from laser light source 46-6 (laser 6) is the non-emphasis narrowband light for the deep blood vessels 70d (deep region 72d). As illustrated in FIGS. 9 and 10, the wavelength of the sixth laser light (L6) that is the non-emphasis narrowband light for the deep blood vessels 70d is 635 nm and is included in the red range 60R.

The first laser light, the fourth laser light, and the sixth laser light are guided in the optical fibers 50-1, 50-4, and 50-6, then enter the optical fiber 54 via the light combiner 52, are guided by the optical fiber 54, and enter the light converter 56 in the distal end of the insertion section 28.

The first laser light, the fourth laser light, and the sixth laser light having entered the light converter 56 in order are converted to have desired light distribution, are then emitted in respective subframes as the illumination light IL, and are radiated to the observation object O.

Note that the light source driver 48 sets the intensity ratio among the first laser light, the fourth laser light, and the sixth laser light in such a manner that mixed light of the first, fourth, and sixth laser light becomes white light. The white light is light in which the color of broadband illumination light IL, such as xenon lamp or halogen lamp, is reproduced. Alternatively, the white light is light that reproduces the color of the observation object O when the observation object O is irradiated with broadband illumination light IL such as a xenon lamp or a halogen lamp. More specifically, the white light is defined using, for example, chromaticity coordinates, a correlated color temperature, or a color difference from a black body locus. For example, the white light is defined as a color within the ranges of (x=0.2 to 0.4, y=0.2 to 0.4) and (x=0.4 to 0.5, y=0.35 to 0.45) in the chromaticity coordinates, a color in the range from 2000 to 100000 k in the correlated color temperature, or a color in the range in which the color difference (duv) from the black body locus is ±0.1 or less in the black body locus. Alternatively, the white light may be defined in consideration of spectral sensitivity of an imaging element. For example, the white light may be defined as described above for the chromaticity coordinates or the correlated color temperature calculated for a spectrum obtained by multiplying the spectrum of the illumination light IL by the spectral sensitivity of the imaging element.

The reflected and scattered light RL of the illumination light IL in the observation object O is detected by the imager 22 that is a monochrome imager.

Here, the first laser light is the laser light of the blue range 60B having the wavelength of 415 nm, and has the reach length up the superficial region 72s. In the case where the first laser light is radiated to the observation object O, the difference between the light intensity in the superficial blood vessels 70s to the reflected and scattered light RL and the light intensity in the vicinity of the superficial blood vessels 70s to the reflected and scattered light RL is large. In other words, the contrast for the superficial blood vessels 70s is high. That is, the superficial blood vessels 70s are emphasized.

Such a wavelength is in synchronization with light emission timing of the first laser light included in the blue range 60B, and the imager 22 detects the reflected and scattered light RL of the first laser light and generates the imaging signal. The imaging signal is output to the image processor 24. As illustrated in FIG. 10, the image processor 24 stores the imaging signal output from the imager 22 to the primary image memory 84 as a primary image signal 94-1. The primary image signal 94-1 will be displayed as an image in which a superficial blood vessel image 96s illustrating the superficial blood vessels 70s is emphasized if the primary image signal 94-1 is displayed on the image display 16 as an image.

Further, the fourth laser light is the laser light of the green range 60G having the wavelength of 515 nm, and has the reach length up to the intermediate region 72m. In the case where the fourth laser light is radiated on the observation object O, the difference between the light intensity in the intermediate blood vessels 70m to the reflected and scattered light RL and the light intensity in the vicinity of the intermediate blood vessels 70m to the reflected and scattered light RL is small. In other words, the contrast for the intermediate blood vessels 70m is low. That is, the intermediate blood vessels 70m are not emphasized.

Such a wavelength is in synchronization with light emission timing of the fourth laser light included in the green range 60G, and the imager 22 detects the reflected and scattered light RL of the fourth laser light and generates the imaging signal. The imaging signal is output to the image processor 24. As illustrated in FIG. 10, the image processor 24 stores the imaging signal output from the imager 22 to the primary image memory 84 as a primary image signal 94-4. The primary image signal 94-4 will be displayed as an image in which an intermediate blood vessel image 96m illustrating the intermediate blood vessels 70m is not emphasized if the primary image signal 94-4 is displayed on the image display 16 as an image.

Further, the sixth laser light is the laser light of the red range 60R having the wavelength of 635 nm, and has the reach length up to the deep region 72d. In the case where the sixth laser light is radiated on the observation object O, the difference between the light intensity in the deep blood vessels 70d to the reflected and scattered light RL and the light intensity in the vicinity of the deep blood vessels 70d to the reflected and scattered light RL is small. In other words, the contrast for the deep blood vessels 70d is low. That is, the deep blood vessels 70d are not emphasized.

Such a wavelength is in synchronization with light emission timing of the sixth laser light included in the red range 60R, and the imager 22 detects the reflected and scattered light RL of the sixth laser light and generates the imaging signal. The imaging signal is output to the image processor 24. As illustrated in FIG. 10, the image processor 24 stores the imaging signal output from the imager 22 to the primary image memory 84 as a primary image signal 94-6. The primary image signal 94-6 will be displayed as an image in which a deep blood vessel image 96d illustrating the deep blood vessels 70d is not emphasized if the primary image signal 94-6 is displayed on the image display 16 as an image.

That is, the light intensity of the illumination light IL in the superficial blood vessels 70s to the reflected and scattered light RL has a larger difference than the light intensity of the illumination light IL in the intermediate blood vessels 70m and in the deep blood vessels 70d to the reflected and scattered light RL, with respect to the light intensity in a surrounding portion of the blood vessels (in a mucous membrane or the like) to the reflected and scattered light RL.

In the illumination light IL in the superficial blood vessel emphasis mode, the superficial region 72s is a depth region of attention, and the intermediate region 72m and the deep region 72d are depth regions of non-attention.

In the case of observing the superficial blood vessels 70s in detail, this emphasis mode is effective.

As described above, the reflected and scattered light RL of the illumination light IL by the laser light source 46-1 (laser 1), the laser light source 46-4 (laser 4), and the laser light source 46-6 (laser 6) is acquired as the primary image signals 94-1, 94-4, and 94-6 in synchronization with the light emission timing of the laser light, and is stored in the primary image memory 84.

When the image selector 86 of the image processor 24 receives the control information according to the superficial blood vessel emphasis mode, the image selector 86 selects primary images to be used from among the primary image signals stored in the primary image memory 84 according to the control information, and sends the selected primary images to the primary intermediate emphasis image generator 90 and the display image generator 92 of the intermediate emphasis image generator 88.

Therefore, in the superficial blood vessel emphasis mode, the image selector 86 sends the primary image signals 94-1, 94-4, and 94-6 acquired in the same radiation cycle and stored in the primary image memory 84 to the display image generator 92. Further, the image selector 86 does not send any of the primary image signals to the primary intermediate emphasis image generator 90.

As illustrated in FIG. 10, the display image generator 92 combines the primary image signals 94-1, 94-4, and 94-6 to generate a display image 98. In this case, the display image generator 92 performs image synthesis processing for the primary image signals 94-1, 94-4, and 94-6 and generates the display image 98 so that the display image 98 is displayed as a so-called color image based on white illumination when displayed on the image display 16 as an observation object image. That is, the image synthesis processing is performed by a known image generation method such as addition processing, where the primary image signal 94-1 is a blue (B) image signal, the primary image signal 94-4 is a green (G) image signal, and the primary image signal 94-6 is a red (R) image signal.

Further, the display image generator 92 may perform image processing for improving visibility. For example, known image processing technologies such as contrast emphasis image processing for narrowing the difference (contrast) between brightness and darkness of an image, contour emphasis image processing for narrowing the difference between brightness and darkness of a contour (edge) portion (boundary of brightness) in the image, vascular structure image processing for suppressing frequency components corresponding to blood vessel patterns can be used.

The display image 98 generated by the image processor 24 in this manner is transmitted to an external monitor that is the image display 16 and is displayed as the observation object image. That is, in the observation object image, the superficial blood vessel image 96s illustrating the superficial blood vessels 70s is highlighted, and the intermediate blood vessel image 96m and the deep blood vessel image 96d illustrating the intermediate blood vessels 70m and deep blood vessels 70d are not highlighted.

As described above, in the superficial blood vessel emphasis mode, the color of the observation object O at the time of observation by the white light is reproduced, and an image in which only the superficial blood vessels 70s are highlighted can be generated by synthesizing the primary image signals 94-1, 94-4, and 94-6 of BGR. Therefore, in the case of observing the superficial blood vessels 70s in detail, this emphasis mode is effective.

In the case of using a color imager having BGR color filters as the imager 22, the laser light source 46-1 (laser 1), the laser light source 46-4 (laser 4), and the laser light source 46-6 (laser 6) may be turned on at the same time rather than turned on in order, and the laser light may be output as white illumination light IL. In this case, a first primary image signal that is a blue image signal in which the superficial blood vessels 70s are emphasized is generated in the B light detection element, a second primary image signal that is a green image signal in which the intermediate blood vessels 70m are not emphasized is generated in the G light detection element, and a third primary image signal that is a red image signal in which the deep blood vessels 70d are not emphasized is generated in the R light detection element, and similar processing is performed for the three primary image signals, whereby the display image 98 can be generated.

Note that, here, as an example of the emphasis mode not to perform intermediate emphasis, the case of the superficial blood vessel emphasis mode of emphasizing the superficial blood vessels 70s has been described. However, the layer to be emphasized is not limited thereto.

FIG. 11 illustrates correspondence of the primary image signals 94-1 to 94-6 (primary images 1 to 6) selectable as BGR color image signals for generating the display image 98. As each of the color image signals, either the emphasis image signal generated by the emphasis narrowband light of corresponding each layer or the non-emphasis image signal generated by the non-emphasis narrowband light of each layer can be selected. The layer using the emphasis image signal is highlighted, and the layer using the non-emphasis image signal is not highlighted.

The primary image signal to be selected can be arbitrarily switched according to the layer to be observed in detail.

The above example has been described as the combinations for reproducing white. However, in the case where no reproduction of white is necessary depending on the purpose of use, not all of the BGR images are used, and for example, only a combination of the B image and the G image may be used. In this case as well, the color is defined using the chromaticity coordinates or the like.

The above is the description about the emphasis mode not to perform intermediate emphasis.

Here, the emphasis mode of performing intermediate emphasis will be described referring back to the flowchart in FIG. 8.

In step S16, when the image selector 86 determines that the emphasis mode is the emphasis mode including intermediate emphasis, the image selector 86 selects part of the primary image signals, that is, two primary image signals. Here, the two primary image signals are one emphasis image signal and one non-emphasis image signal by the laser light with a wavelength included in the same color range. Then, the display image generator 92 synthesizes the selected two primary image signals stored in the primary image memory 84 by the synthesis ratio indicated by the control information set in step 13 to generate a primary intermediate emphasis image signal (step S19).

In addition, the image selector 86 selects the remaining primary image signals. That is, the image selector 86 selects two primary image signals. Here, the two primary image signals are one emphasis image signal and one non-emphasis image signal by the laser light with wavelengths included in color ranges different from the color range used for generation of the primary intermediate emphasis image signal and in color ranges different from each other. Then, the display image generator 92 synthesizes the primary intermediate emphasis image signal generated in step S19 and the selected two primary image signals stored in the primary image memory 84 by the synthesis method and the synthesis ratio indicated by the control information set in step S13 to generate a display image that is an intermediate emphasis image (step S20).

The image display 16 displays the display image as an observation object image (step S18).

Here, as an example of the emphasis mode including intermediate emphasis, a superficial blood vessel emphasis-intermediate blood vessel intermediate emphasis mode will be described.

<Superficial Blood Vessel Emphasis-Intermediate Blood Vessel Intermediate Emphasis Mode>

This superficial blood vessel emphasis-intermediate blood vessel intermediate emphasis mode is used in the case of observing a state of the intermediate blood vessels 70m at the same time while focusing on the superficial blood vessels 70s. In detailed diagnosis of lesions, a layer to be observed in detail and another layer are acquired at the same time, whereby the visibility of the layer particularly required for a detailed observation can be improved and the layer can be diagnosed while confirming the state of the another layer.

When the superficial blood vessel emphasis-intermediate blood vessel intermediate emphasis mode is input to the input device 18 by the user as the emphasis mode, the light source output pattern information and the control information according to the superficial blood vessel emphasis-intermediate blood vessel intermediate emphasis mode are output from the emphasis mode setting unit 26 to the light source driver 48 of the illuminator 20 and the image selector 86 of the image processor 24.

When the light source driver 48 receives the light source output pattern information according to the superficial blood vessel emphasis-intermediate blood vessel intermediate emphasis mode, the light source driver 48 repeatedly turns on the laser light source 46-1 (laser 1), the laser light source 46-3 (laser 3), the laser light source 46-4 (laser 4), and the laser light source 46-6 (laser 6) in that order as one cycle of radiation to cause the laser light sources 46-1, 46-3, 46-4, and 46-6 to emit the first laser light, the third laser light, the fourth laser light, and the sixth laser light in order, as illustrated in FIG. 12. That is, one frame period that is a typical acquisition period of an imaging signal is divided into four subframe periods, as illustrated in FIG. 12, one laser light source is turned on in each subframe, and the laser light source to be turned on is sequentially switched in each subframe.

Here, the laser light source 46-1 (laser 1) is the emphasis narrowband light source for the superficial blood vessels 70s (superficial region 72s), and the first laser light emitted from laser light source 46-1 (laser 1) is the emphasis narrowband light for the superficial blood vessels 70s (superficial region 72s). As illustrated in FIGS. 12 and 13, the wavelength of the first laser light (L1) that is the emphasis narrowband light for the superficial blood vessels 70s is 415 nm and is included in the blue range 60B. Note that, in FIG. 13, the vertical axis of the laser light spectrum is drawn in an arbitrary scale.

Further, the laser light source 46-3 (laser 3) is the emphasis narrowband light source for the intermediate blood vessels 70m (intermediate region 72m), and the third laser light emitted from laser light source 46-3 (laser 3) is the emphasis narrowband light for the intermediate blood vessels 70m (intermediate region 72m). As illustrated in FIGS. 12 and 13, the wavelength of the third laser light (L3) that is the emphasis narrowband light corresponding to the intermediate blood vessels 70m is 540 nm and is included in the green range 60G.

Further, the laser light source 46-4 (laser 4) is the non-emphasis narrowband light source for the intermediate blood vessels 70m (intermediate region 72m), and the fourth laser light emitted from laser light source 46-4 (laser 4) is the non-emphasis narrowband light for the intermediate blood vessels 70m (intermediate region 72m). As illustrated in FIGS. 12 and 13, the wavelength of the fourth laser light (L4) that is the non-emphasis narrowband light for the intermediate blood vessels 70m is 515 nm and is included in the green range 60G.

Then, the laser light source 46-6 (laser 6) is the non-emphasis narrowband light source for the deep blood vessels 70d (deep region 72d), and the sixth laser light emitted from laser light source 46-6 (laser 6) is the non-emphasis narrowband light for the deep blood vessels 70d (deep region 72d). As illustrated in FIGS. 12 and 13, the wavelength of the sixth laser light (L6) that is the non-emphasis narrowband light for the deep blood vessels 70d is 635 nm and is included in the red range 60R.

The first laser light, the third laser light, the fourth laser light, and the sixth laser light are guided in the optical fibers 50-1, 50-4, and 50-6, then enter the optical fiber 54 via the light combiner 52, are guided by the optical fiber 54, and enter the light converter 56 in the distal end of the insertion section 28.

The first laser light, the third laser light, the fourth laser light, and the sixth laser light having entered the light converter 56 in order are converted to have desired light distribution, are then emitted in respective subframes as the illumination light IL, and are radiated to the observation object O.

Note that the light source driver 48 sets the intensity ratio among the first laser light, the third laser light, the fourth laser light, and the sixth laser light in such a manner that mixed light of the first, third, fourth, and sixth laser light becomes white light.

The reflected and scattered light RL of the illumination light IL in the observation object O is detected by the imager 22 that is a monochrome imager.

Here, the first laser light is the laser light of the blue range 60B having the wavelength of 415 nm, and has the reach length up the superficial region 72s. In the case where the first laser light is radiated to the observation object O, the difference between the light intensity in the superficial blood vessels 70s to the reflected and scattered light RL and the light intensity in the vicinity of the superficial blood vessels 70s to the reflected and scattered light RL is large. In other words, the contrast for the superficial blood vessels 70s is high. That is, the superficial blood vessels 70s are emphasized.

Such a wavelength is in synchronization with light emission timing of the first laser light included in the blue range 60B, and the imager 22 detects the reflected and scattered light RL of the first laser light and generates the imaging signal. The imaging signal is output to the image processor 24. As illustrated in FIG. 13, the image processor 24 stores the imaging signal output from the imager 22 to the primary image memory 84 as the primary image signal 94-1. The primary image signal 94-1 will be displayed as an image in which a superficial blood vessel image 96s illustrating the superficial blood vessels 70s is emphasized if the primary image signal 94-1 is displayed on the image display 16 as an image.

Further, the third laser light is the laser light of the green range 60G having the wavelength of 540 nm, and has the reach length up to the intermediate region 72m. In the case where the third laser light is radiated on the observation object O, the difference between the light intensity in the intermediate blood vessels 70m to the reflected and scattered light RL and the light intensity in the vicinity of the intermediate blood vessels 70m to the reflected and scattered light RL is large. In other words, the contrast for the intermediate blood vessels 70m is high. That is, the intermediate blood vessels 70m are emphasized.

Such a wavelength is in synchronization with light emission timing of the third laser light included in the green range 60G, and the imager 22 detects the reflected and scattered light RL of the third laser light and generates the imaging signal. The imaging signal is output to the image processor 24. As illustrated in FIG. 13, the image processor 24 stores the imaging signal output from the imager 22 to the primary image memory 84 as the primary image signal 94-3. The primary image signal 94-3 will be displayed as an image in which the intermediate blood vessel image 96m illustrating the intermediate blood vessels 70m is emphasized if the primary image signal 94-3 is displayed on the image display 16 as an image.

Further, the fourth laser light is the laser light of the green range 60G having the wavelength of 515 nm, and has the reach length up to the intermediate region 72m. In the case where the fourth laser light is radiated on the observation object O, the difference between the light intensity in the intermediate blood vessels 70m to the reflected and scattered light RL and the light intensity in the vicinity of the intermediate blood vessels 70m to the reflected and scattered light RL is small. In other words, the contrast for the intermediate blood vessels 70m is low. That is, the intermediate blood vessels 70m are not emphasized.

Such a wavelength is in synchronization with light emission timing of the fourth laser light included in the green range 60G, and the imager 22 detects the reflected and scattered light RL of the fourth laser light and generates the imaging signal. The imaging signal is output to the image processor 24. As illustrated in FIG. 13, the image processor 24 stores the imaging signal output from the imager 22 to the primary image memory 84 as the primary image signal 94-4. The primary image signal 94-4 will be displayed as an image in which an intermediate blood vessel image 96m illustrating the intermediate blood vessels 70m is not emphasized if the primary image signal 94-4 is displayed on the image display 16 as an image.

Further, the sixth laser light is the laser light of the red range 60R having the wavelength of 635 nm, and has the reach length up to the deep region 72d. In the case where the sixth laser light is radiated on the observation object O, the difference between the light intensity in the deep blood vessels 70d to the reflected and scattered light RL and the light intensity in the vicinity of the deep blood vessels 70d to the reflected and scattered light RL is small. In other words, the contrast for the deep blood vessels 70d is low. That is, the deep blood vessels 70d are not emphasized.

Such a wavelength is in synchronization with light emission timing of the sixth laser light included in the red range 60R, and the imager 22 detects the reflected and scattered light RL of the sixth laser light and generates the imaging signal. The imaging signal is output to the image processor 24. As illustrated in FIG. 13, the image processor 24 stores the imaging signal output from the imager 22 to the primary image memory 84 as the primary image signal 94-6. The primary image signal 94-6 will be displayed as an image in which a deep blood vessel image 96d illustrating the deep blood vessels 70d is not emphasized if the primary image signal 94-6 is displayed on the image display 16 as an image.

That is, the light intensity of the illumination light IL in the superficial blood vessels 70s to the reflected and scattered light RL has a larger difference than the light intensity of the illumination light IL in the intermediate blood vessels 70m to the reflected and scattered light RL, with respect to the light intensity in a surrounding portion of the blood vessels (in a mucous membrane or the like) to the reflected and scattered light RL. Further, the light intensity of the illumination light IL in the intermediate blood vessels 70m to the reflected and scattered light RL has a larger difference than the light intensity of the illumination light IL in the deep blood vessels 70d to the reflected and scattered light RL, with respect to the light intensity in a surrounding portion of the blood vessels (in a mucous membrane or the like) to the reflected and scattered light RL.

As described above, the reflected and scattered light RL of the illumination light IL by the laser light source 46-1 (laser 1), the laser light source 46-3 (laser 3), the laser light source 46-4 (laser 4), and the laser light source 46-6 (laser 6) is acquired as the primary image signals 94-1, 94-3, 94-4, and 94-6 in synchronization with the light emission timing of the laser light, and is stored in the primary image memory 84.

When the image selector 86 of the image processor 24 receives the control information according to the superficial blood vessel emphasis mode, the image selector 86 selects primary images to be used from among the primary image signals stored in the primary image memory 84 according to the control information, and sends the selected primary images to the primary intermediate emphasis image generator 90 and the display image generator 92 of the intermediate emphasis image generator 88.

Therefore, in the superficial blood vessel emphasis-intermediate blood vessel intermediate emphasis mode, the image selector 86 sends the primary image signals 94-3 and 94-4 acquired in the same radiation cycle and stored in the primary image memory 84 to the primary intermediate emphasis image generator 90. Further, the image selector 86 sends the primary image signals 94-1 and 94-6 acquired in the same radiation cycle and stored in the primary image memory 84 to the display image generator 92.

As illustrated in FIG. 13, the primary intermediate emphasis image generator 90 synthesizes the primary image signal 94-3 and the primary image signal 94-4 by weighted average of each pixel to generate a primary intermediate emphasis image signal 100. To be specific, in step S19, the primary intermediate emphasis image generator 90 executes the processing illustrated in the flowchart in FIG. 14.

That is, the primary intermediate emphasis image generator 90 copies one of the primary image signal 94-3 and the primary image signal 94-4 (hereinafter referred to as a first primary image signal) to an internal memory (not illustrated), and generates the primary intermediate emphasis image signal 100 (step S191).

Next, the primary intermediate emphasis image generator 90 reads a luminance value of a pixel of attention from the first primary image signal (step S192), and reads a luminance value of a pixel of attention from the other (hereinafter referred to as second primary image signal) of the primary image signal 94-3 and the primary image signal 94-4 (step S193). Then, the primary intermediate emphasis image generator 90 weights and averages the read luminance values (step S194), and replaces a luminance value of a corresponding pixel of the primary intermediate emphasis image signal 100 generated in the memory (not illustrated) with the weighted average result (step S195).

After that, the primary intermediate emphasis image generator 90 determines the existence or non-existence of an unprocessed pixel (step S196). If there is an unprocessed pixel, the primary intermediate emphasis image generator 90 returns to step S192 and repeats the processing for the next pixel of attention.

In this manner, the processing from step S192 to S195 is repeated until the processing for all the pixels is completed. When the processing for all the pixels is completed, the primary intermediate emphasis image signal 100 obtained by weighting and averaging the primary image signal 94-3 and the primary image signal 94-4 is stored in the internal memory (not illustrated) of the primary intermediate emphasis image generator 90.

Both the primary image signal 94-3 and the primary image signal 94-4 have the reach length up to the intermediate region 72m and are image signals of the green range 60G, capable of reproducing white light in combination with the primary image signal 94-1 and the primary image signal 94-6. However, the contrast of the intermediate blood vessels 70m differs. By the synthesis by weighted average, the primary intermediate emphasis image signal 100 of the intermediate blood vessels 70m, in which the contrast of the intermediate blood vessel 70m portion is an intermediate between the primary image signal 94-3 and the primary image signal 94-4, can be generated while maintaining the brightness and the color of the mucous membrane and the like other than the intermediate blood vessels 70m.

Note that weighting of the weighted average is set according to the control information of the superficial blood vessel emphasis mode. The weighting of the weighted average is, for example, 1:1 for the primary image signal 94-3:the primary image signal 94-4.

The weighting may be able to be arbitrarily set by an input from the input device 18 by the user. To increase the degree of emphasis, the primary image signal 94-3 is weighted. To decrease the degree of emphasis, the primary image signal 94-4 is weighted.

The primary intermediate emphasis image generator 90 sends the primary intermediate emphasis image signal 100 of the intermediate blood vessels 70m generated in this manner to the display image generator 92.

As illustrated in FIG. 13, the display image generator 92 combines the primary intermediate emphasis image signal 100 and the primary image signals 94-1 and 94-6, which have been acquired in the same radiation cycle as the base primary image signals 94-3 and 94-4, to generate the display image 98 as an intermediate emphasis image. In this case, the display image generator 92 performs image synthesis processing for the primary image signals 94-1, the primary intermediate emphasis image signal 100, and the primary image signal 94-6 and generates the display image 98 that is an intermediate emphasis image so that the display image 98 is displayed as a so-called color image based on white illumination when displayed on the image display 16 as an observation object image. That is, the image synthesis processing is performed by a known image generation method such as addition processing, where the primary image signal 94-1 is a blue (B) image signal, the primary intermediate emphasis image signal 100 is a green (G) image signal, and the primary image signal 94-6 is a red (R) image signal.

Further, the display image generator 92 may perform image processing for improving visibility. For example, known image processing technologies such as contrast emphasis image processing for narrowing the difference (contrast) between brightness and darkness of an image, contour emphasis image processing for narrowing the difference between brightness and darkness of a contour (edge) portion (boundary of brightness) in the image, vascular structure image processing for suppressing frequency components corresponding to blood vessel patterns can be used.

The display image 98 that is an intermediate emphasis image generated by the image processor 24 in this manner is transmitted to an external monitor that is the image display 16 and is displayed as the observation object image.

That is, in this observation object image, the superficial blood vessels 70s are highlighted as the superficial blood vessel image 96s, as in the superficial blood vessel emphasis mode, and the deep blood vessel image 96d illustrating the deep blood vessels 70d is not highlighted.

On the other hand, in the superficial blood vessel emphasis-intermediate blood vessel intermediate emphasis mode, the primary image signal 94-3 acquire when the third laser light that emphasizes the intermediate blood vessels 70m is radiated to the observation object O and the primary image signal 94-4 acquired when the fourth laser light that does not emphasizes the intermediate blood vessels 70m is radiated to the observation object O are weighted and averaged, whereby the primary intermediate emphasis image signal 100 is generated. Therefore, the intermediate blood vessels 70m are highlighted at an intermediate level between a state where only the third laser light is radiated and the intermediate blood vessels 70m are emphasized and a state where only the fourth laser light is radiated and the intermediate blood vessels 70m are not emphasized.

As described above, in the superficial blood vessel emphasis-intermediate blood vessel intermediate emphasis mode, the BR primary image signals 94-1 and 94-6 and the G primary intermediate emphasis image signal 100 are synthesized, whereby the color of the observation object O at the time of observation with white light can be reproduced, and the image in which superficial blood vessels 70s are emphasized and the intermediate blood vessels 70m are intermediately emphasized can be generated. Therefore, in the case of observing the state of the intermediate blood vessels 70m while observing the superficial blood vessels 70s in detail, this emphasis mode is effective.

In the case of using a color imager having BGR color filters as the imager 22, for example, a lighting method of alternately repeating lighting of the laser light source 46-1 (laser 1), the laser light source 46-4 (laser 4), and the laser light source 46-6 (laser 6), and lighting of the laser light source 46-3 (laser 3) as one radiation cycle may be employed. In this case, an equivalent image synthesis processing can be performed by acquiring the primary image signal 94-1 in the B light detection element, the primary image signal 94-4 in the G light detection element, and the primary image signal 94-6 in the R light detection element at the time of lighting the laser light source 46-1 (laser 1), the laser light source 46-4 (laser 4), and the laser light source 46-6 (laser 6), and acquiring the primary image signal 94-3 in the G light detection element at the time of lighting the laser light source 46-3 (laser 3).

Note that, here, the case of the superficial blood vessel emphasis-intermediate blood vessel intermediate emphasis mode of emphasizing the superficial blood vessels 70s and intermediately emphasize the intermediate blood vessels 70m has been described as an example of the emphasis mode of performing intermediate emphasis. However, the layer to be emphasized and the layer to be intermediately emphasized are not limited thereto.

For example, there is a superficial and intermediate blood vessel intermediate emphasis-deep blood vessel emphasis mode of intermediately emphasizing the superficial blood vessels and the intermediate blood vessels, and to emphasize the deep blood vessels. In the case where the user selects this emphasis mode from the input device 18, the laser light source 46-1 (laser 1), the laser light source 46-2 (laser 2), the laser light source 46-3 (laser 3), the laser light source 46-4 (laser 4), and the laser light source 46-5 (laser 5) are caused to emit light, and the primary image signal 94-1, the primary image signal 94-2, the primary image signal 94-3, the primary image signal 94-4, and the primary image signal 94-5 are acquired. Then, the primary intermediate emphasis image signal of the surface is generated from the primary image signal 94-1 and the primary image signal 94-2, the primary intermediate emphasis image signal of the intermediate layer is generated from the primary image signal 94-3 and the primary image signal 94-4, and the display image 98 that is an intermediate emphasis image is generated from the primary intermediate emphasis image signals of the surface and of the intermediate layer, and the primary image signal 94-5. In the superficial and intermediate blood vessel intermediate emphasis-deep blood vessel emphasis mode, the display image 98 in which the degree of emphasis of the deep blood vessels 70d is strong and the degrees of emphasis of the superficial blood vessels 70s and the intermediate blood vessels 70m are weak can be obtained, and the deep blood vessels 70d can be easily observed.

Further, the synthesis of the emphasis image signal and the non-emphasis image signal in generation of the primary intermediate emphasis image signal is not necessarily performed by weighted average. For example, addition may be made so that the observation object other than the blood vessels becomes brighter than an average brightness of the emphasis image signal and the non-emphasis image signal.

Other than the above example, emphasis can be performed by using a primary image signal generated with the reflected and scattered light RL of the emphasis narrowband light in any of the surface, the intermediate surface, and the deep surface, as a corresponding color image signal of display image synthesis. Further, similarly, intermediate emphasis can be performed by synthesizing a primary image signal generated with the reflected and scattered light RL of the emphasis narrowband light and a primary image signal generated with the reflected and scattered light RL of the non-emphasis narrowband light to generate a primary intermediate emphasis image signal, and using the primary intermediate emphasis image signal as a corresponding color image signal of display image synthesis.

Figure 14:
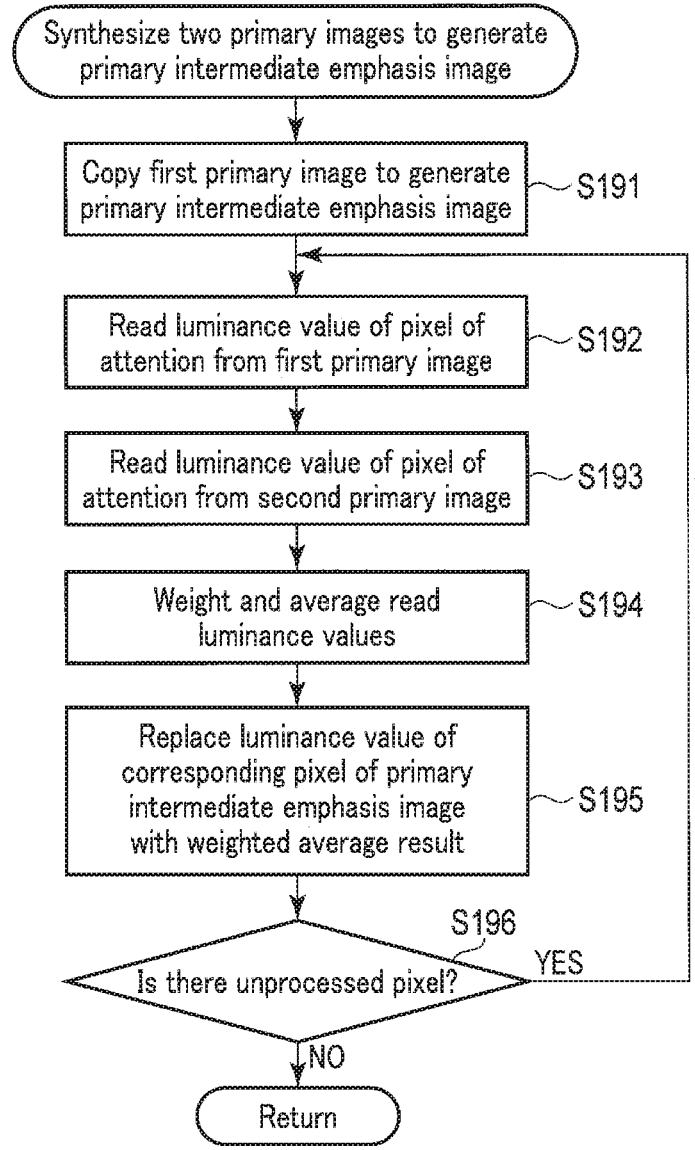
FIG. 14 is a flowchart for describing details of a subroutine for synthesizing two primary images in FIG. 8 to generate a primary intermediate emphasis image.

FIG. 14 illustrates correspondence of the primary image signals 94-1 to 94-6 (primary images 1 to 6) selectable as BGR color image signals for generating the display image 98 that is an intermediate emphasis image. As each of the color image signals, any of the emphasis image signal generated by the emphasis narrowband light of corresponding each layer, the non-emphasis image signal generated by the non-emphasis narrowband light of each layer, and the primary intermediate emphasis image signal obtained by synthesizing the emphasis image signal and the non-emphasis image signal can be selected. The layer using the emphasis image signal is highlighted, the layer using the non-emphasis image signal is not highlighted, and the layer using the primary intermediate emphasis image signal is intermediately emphasized.

The primary image signal and the primary intermediate emphasis image signal to be selected can be arbitrarily switched according to the purpose of use.

For example, when performing endoscopic surgery, it is necessary to resect a lesion without damaging a thick blood vessel in the deep layer. In that case, the primary intermediate emphasis image signal of the surface is used as a B image signal, the primary intermediate emphasis image signal of the intermediate layer is used as a G image signal, and the primary image signal that is an emphasis image signal of the deep layer is used as an R image, whereby the deep blood vessel emphasis-superficial and intermediate blood vessel intermediate emphasis mode can be set. This emphasis mode especially focuses on the deep layer while confirming the blood vessels as a whole. Therefore, an observation in which the degrees of emphasis of the surface and the intermediate layer can be performed.

Further, for example, the primary intermediate emphasis image signal of the surface is used as the B image signal, the primary intermediate emphasis image signal of the intermediate layer is used as the G image signal, and the primary intermediate emphasis image signal of the deep layer is used as the R image signal, whereby a superficial, intermediate, and deep blood vessel intermediate emphasis mode can be set. In the endoscopic examination, an image becomes complicated if too highlighted in areas where blood vessels are densely packed, and the visibility may be perversely reduced. In this emphasis mode, an observation in which all the layers are adjusted to emphasis levels that are easy for the user to see is possible. The balance of the degrees of emphasis of the layers can also be arbitrarily adjusted by weighting and synthesizing the emphasis image signal and the non-emphasis image signal.

The radiation pattern of layers used for acquisition of the primary image signals in each emphasis mode, the primary image signal used for generation of the primary intermediate emphasis image signal, the primary image signal used for generation of the display image, and the method of synthesizing the image signals are stored in the emphasis mode storage 78 of the emphasis mode setting unit 26. Then, the primary image signals are selected according to image acquisition timing synchronized with the radiation pattern so that the intermediate emphasis image is generated by the primary image signals acquired from laser wavelengths having the same color range (depth region) in the same radiation cycle.

The above-described emphasis mode has been described as an example. However, the emphasis mode is not limited thereto, and the emphasis mode can be adjusted to an arbitrary emphasis mode according to the state of the observation object O or the layer to be focused by adjusting emphasis, non-emphasis, and intermediate emphasis of an arbitrary layer and the level of the intermediate emphasis.

For example, the endoscope apparatus 10 according to the present embodiment has the following sixteen emphasis modes according to observation purposes, and the user inputs an emphasis mode of performing an observation by the input device 18.

The sixteen emphasis modes (emphasis modes M1 to M16) possessed by the endoscope apparatus 10 are as follows, as illustrated in FIG. 16.

The emphasis mode M1 (superficial blood vessel emphasis mode) is a mode of highlighting only blood vessels located in the surface of the observation object O. In the emphasis mode M1, in the case where the imager 22 is a monochrome imager, the laser light source 46-1 (laser 1) that is the emphasis narrowband light source for the superficial blood vessels, the laser light source 46-4 (laser 4) that is the non-emphasis narrowband light source for the intermediate blood vessels, and the laser light source 46-6 (laser 6) that is the non-emphasis narrowband light source for the deep blood vessels are turned on in order in the same radiation cycle. Then, the display image 98 in which only the superficial blood vessel image 96s illustrating the superficial blood vessels 70s is highlighted is generated by combining a primary image signal that is an emphasis image signal of the surface, a primary image signal that is a non-emphasis image signal of the intermediate layer, and a primary image signal that is a non-emphasis image signal of the deep layer.

The emphasis mode M2 (intermediate blood vessel emphasis mode) is a mode of highlighting only blood vessels located in an intermediate layer of the observation object O. In the emphasis mode M2, in the case where the imager 22 is a monochrome imager, the laser light source 46-2 (laser 2) that is the non-emphasis narrowband light source for the superficial blood vessels, the laser light source 46-3 (laser 3) that is the emphasis narrowband light source for the intermediate blood vessels, and the laser light source 46-6 (laser 6) that is the non-emphasis narrowband light source for the deep blood vessels are turned on in order in the same radiation cycle. Then, the display image 98 in which only the intermediate blood vessel image 96m illustrating the intermediate blood vessels 70m is highlighted is generated by combining a primary image signal that is a non-emphasis image signal of the surface, a primary image signal that is an emphasis image signal of the intermediate layer, and the primary image signal that is a non-emphasis image signal of the deep layer.

The emphasis mode M3 (deep blood vessel emphasis mode) is a mode of highlighting only blood vessels located in a deep layer of the observation object O. In the emphasis mode M3, in the case where the imager 22 is a monochrome imager, the laser light source 46-2 (laser 2) that is the non-emphasis narrowband light source for the superficial blood vessels, the laser light source 46-4 (laser 4) that is the non-emphasis narrowband light source for the intermediate blood vessels, and the laser light source 46-5 (laser 5) that is the emphasis narrowband light source for the deep blood vessels are turned on in order in the same radiation cycle. Then, the display image 98 in which only the deep blood vessel image 96d illustrating the deep blood vessels 70d is highlighted is generated by combining the primary image signal that is a non-emphasis image signal of the surface, the primary image signal that is a non-emphasis image signal of the intermediate layer, and a primary image signal that is an emphasis image signal of the deep layer.

The emphasis mode M4 (superficial blood vessel emphasis-intermediate blood vessel intermediate emphasis mode) is a mode of highlighting the blood vessels located in the surface of the observation object O and to intermediately emphasize the blood vessels located in the intermediate layer. In the emphasis mode M4, in the case where the imager 22 is a monochrome imager, the laser light source 46-1 (laser 1) that is the emphasis narrowband light source for the superficial blood vessels, the laser light source 46-3 (laser 3) that is the emphasis narrowband light source for the intermediate blood vessels, the laser light source 46-4 (laser 4) that is the non-emphasis narrowband light source for the intermediate blood vessels, and the laser light source 46-6 (laser 6) that is the non-emphasis narrowband light source for the deep blood vessels are turned on in order in the same radiation cycle. Then, a primary intermediate emphasis image signal of the intermediate layer is generated by weighting and averaging the primary image signal that is an emphasis image signal of the intermediate layer and the primary image signal that is a non-emphasis image signal of the intermediate layer, and an intermediate emphasis image in which the superficial blood vessel image 96s illustrating the superficial blood vessels 70s is highlighted, and the intermediate blood vessel image 96m illustrating the intermediate blood vessels 70m is intermediately highlighted is generated as the display image 98 by combining the primary intermediate emphasis image signal of the intermediate layer, the primary image signal that is an emphasis image signal of the surface, and the primary image signal that is a non-emphasis image signal of the deep layer.

The emphasis mode M5 (superficial blood vessel intermediate emphasis-intermediate blood vessel emphasis mode) is a mode of intermediately emphasizing the blood vessels located in the surface of the observation object O and to highlight the blood vessels located in the intermediate layer. In the emphasis mode M5, in the case where the imager 22 is a monochrome imager, the laser light source 46-1 (laser 1) that is the emphasis narrowband light source for the superficial blood vessels, the laser light source 46-2 (laser 2) that is the non-emphasis narrowband light source for the superficial blood vessel, the laser light source 46-3 (laser 3) that is the emphasis narrowband light source for the intermediate blood vessels, and the laser light source 46-6 (laser 6) that is the non-emphasis narrowband light source for the deep blood vessels are turned on in order in the same radiation cycle. Then, a primary intermediate emphasis image signal of the surface is generated by weighting and averaging the primary image signal that is an emphasis image signal of the surface and the primary image signal that is a non-emphasis image signal of the surface, and an intermediate emphasis image in which the intermediate blood vessel image 96m illustrating the intermediate blood vessels 70m is highlighted, and the superficial blood vessel image 96s illustrating the superficial blood vessels 70s is intermediately highlighted is generated as the display image 98 by combining the primary intermediate emphasis image signal of the surface, the primary image signal that is an emphasis image signal of the intermediate surface, and the primary image signal that is a non-emphasis image signal of the deep layer.

The emphasis mode M6 (superficial blood vessel emphasis-deep blood vessel intermediate emphasis mode) is a mode of highlighting the blood vessels located in the surface of the observation object O and to intermediately emphasize the blood vessels located in the deep layer. In the emphasis mode M6, in the case where the imager 22 is a monochrome imager, the laser light source 46-1 (laser 1) that is the emphasis narrowband light source for the superficial blood vessels, the laser light source 46-4 (laser 4) that is the non-emphasis narrowband light source for the intermediate blood vessels, the laser light source 46-5 (laser 5) that is the emphasis narrowband light source for the deep blood vessels, and the laser light source 46-6 (laser 6) that is the non-emphasis narrowband light source for the deep blood vessels are turned on in order in the same radiation cycle. Then, a primary intermediate emphasis image signal of the deep layer is generated by weighting and averaging the primary image signal that is an emphasis image signal of the deep layer and the primary image signal that is a non-emphasis image signal of the deep layer, and an intermediate emphasis image in which the superficial blood vessel image 96s illustrating the superficial blood vessels 70s is highlighted and the deep blood vessel image 96d illustrating the deep blood vessels 70d is intermediately highlighted is generated as the display image 98 by combining the primary intermediate emphasis image signal of the deep layer, the primary image signal that is an emphasis image signal of the surface, and the primary image signal that is a non-emphasis image signal of the intermediate layer.

The emphasis mode M7 (superficial blood vessel intermediate emphasis-deep blood vessel emphasis mode) is a mode of highlighting the blood vessels located in the deep layer of the observation object O and to intermediately emphasize the blood vessels located in the surface. In the emphasis mode M7, in the case where the imager 22 is a monochrome imager, the laser light source 46-1 (laser 1) that is the emphasis narrowband light source for the superficial blood vessels, the laser light source 46-2 (laser 2) that is the non-emphasis narrowband light source for the superficial blood vessel, the laser light source 46-4 (laser 4) that is the non-emphasis narrowband light source for the intermediate blood vessels, and the laser light source 46-5 (laser 5) that is the emphasis narrowband light source for the deep blood vessels are turned on in order in the same radiation cycle. Then, a primary intermediate emphasis image signal of the surface is generated by weighting and averaging the primary image signal that is an emphasis image signal of the surface and the primary image signal that is a non-emphasis image signal of the surface, and an intermediate emphasis image in which the deep blood vessel image 96d illustrating the deep blood vessels 70d is highlighted and the superficial blood vessel image 96s illustrating the superficial blood vessels 70s is intermediately highlighted is generated as the display image 98 by combining the primary intermediate emphasis image signal of the surface, the primary image signal that is a non-emphasis image signal of the intermediate layer, and the primary image signal that is an emphasis image signal of the deep layer.

The emphasis mode M8 (intermediate blood vessel emphasis-deep blood vessel intermediate emphasis mode) is a mode of highlighting the blood vessels located in the intermediate layer of the observation object O and to intermediately emphasize the blood vessels located in the deep layer. In the emphasis mode M8, in the case where the imager 22 is a monochrome imager, the laser light source 46-2 (laser 2) that is the non-emphasis narrowband light source for the superficial blood vessels, the laser light source 46-3 (laser 3) that is the emphasis narrowband light source for the intermediate blood vessels, the laser light source 46-5 (laser 5) that is the emphasis narrowband light source for the deep blood vessels, and the laser light source 46-6 (laser 6) that is the non-emphasis narrowband light source for the deep blood vessels are turned on in order in the same radiation cycle. Then, a primary intermediate emphasis image signal of the deep layer is generated by weighting and averaging the primary image signal that is an emphasis image signal of the deep layer and the primary image signal that is a non-emphasis image signal of the deep layer, and an intermediate emphasis image in which the intermediate blood vessel image 96m illustrating the intermediate blood vessels 70m is highlighted and the deep blood vessel image 96d illustrating the deep blood vessels 70d is intermediately highlighted is generated as the display image 98 by combining the primary intermediate emphasis image signal of the deep layer, the primary image signal that is a non-emphasis image signal of the surface, and the primary image signal that is an emphasis image signal of the intermediate layer.

The emphasis mode M9 (intermediate blood vessel intermediate emphasis-deep blood vessel emphasis mode) is a mode of intermediately highlighting the blood vessels located in the intermediate layer of the observation object O and to emphasize the blood vessels located in the deep layer. In the emphasis mode M9, in the case where the imager 22 is a monochrome imager, the laser light source 46-2 (laser 2) that is the non-emphasis narrowband light source for the superficial blood vessels, the laser light source 46-3 (laser 3) that is the emphasis narrowband light source for the intermediate blood vessels, the laser light source 46-4 (laser 4) that is the non-emphasis narrowband light source for the intermediate blood vessels, and the laser light source 46-5 (laser 5) that is the emphasis narrowband light source for the deep blood vessels are turned on in order in the same radiation cycle. Then, a primary intermediate emphasis image signal of the intermediate layer is generated by weighting and averaging the primary image signal that is an emphasis image signal of the intermediate layer and the primary image signal that is a non-emphasis image signal of the intermediate layer, and an intermediate emphasis image in which the deep blood vessel image 96d illustrating the deep blood vessels 70d is highlighted and the intermediate blood vessel image 96m illustrating the intermediate blood vessels 70m is intermediately highlighted is generated as the display image 98 by combining the primary intermediate emphasis image signal of the intermediate layer, the primary image signal that is a non-emphasis image signal of the surface, and the primary image signal that is an emphasis image signal of the deep layer.

The emphasis mode M10 (superficial blood vessel emphasis-intermediate and deep blood vessel intermediate emphasis mode) is a mode of highlighting the blood vessels located in the surface of the observation object O, and to intermediately emphasize the blood vessels located in the intermediate layer and to intermediately emphasize the blood vessels located in the deep layer. In the emphasis mode M10, in the case where the imager 22 is a monochrome imager, the laser light source 46-1 (laser 1) that is the emphasis narrowband light source for the superficial blood vessels, the laser light source 46-3 (laser 3) that is the emphasis narrowband light source for the intermediate blood vessels, the laser light source 46-4 (laser 4) that is the non-emphasis narrowband light source for the intermediate blood vessels, the laser light source 46-5 (laser 5) that is the emphasis narrowband light source for the deep blood vessels, and the laser light source 46-6 (laser 6) that is the non-emphasis narrowband light source for the deep blood vessels are turned on in order in the same radiation cycle. Then, a primary intermediate emphasis image signal of the intermediate layer is generated by weighting and averaging the primary image signal that is an emphasis image signal of the intermediate layer and the primary image signal that is a non-emphasis image signal of the intermediate layer, and a primary intermediate emphasis image signal of the deep layer is generated by weighting and averaging the primary image signal that is an emphasis image signal of the deep layer and the primary image signal that is a non-emphasis image signal of the deep layer, and an intermediate emphasis image in which the superficial blood vessel image 96s illustrating the superficial blood vessels 70s is highlighted, and the intermediate blood vessel image 96m illustrating the intermediate blood vessels 70m and the deep blood vessel image 96d illustrating the deep blood vessels 70d are intermediately highlighted is generated as the display image 98 by combining the primary intermediate emphasis image signals of the intermediate layer and of the deep layer, and the primary image signal that is an emphasis image signal of the surface.

The emphasis mode M11 (intermediate and deep blood vessel intermediate emphasis mode) is a mode of intermediately emphasizing the blood vessels located in the intermediate layer of the observation object O and to intermediately emphasize the blood vessels located in the deep layer. In the emphasis mode M11, in the case where the imager 22 is a monochrome imager, the laser light source 46-2 (laser 2) that is the non-emphasis narrowband light source for the superficial blood vessels, the laser light source 46-3 (laser 3) that is the emphasis narrowband light source for the intermediate blood vessels, the laser light source 46-4 (laser 4) that is the non-emphasis narrowband light source for the intermediate blood vessels, the laser light source 46-5 (laser 5) that is the emphasis narrowband light source for the deep blood vessels, and the laser light source 46-6 (laser 6) that is the non-emphasis narrowband light source for the deep blood vessels are turned on in order in the same radiation cycle. Then, a primary intermediate emphasis image signal of the intermediate layer is generated by weighting and averaging the primary image signal that is an emphasis image signal of the intermediate layer and the primary image signal that is a non-emphasis image signal of the intermediate layer, and a primary intermediate emphasis image signal of the deep layer is generated by weighting and averaging the primary image signal that is an emphasis image signal of the deep layer and the primary image signal that is a non-emphasis image signal of the deep layer, an intermediate emphasis image in which the intermediate blood vessel image 96m illustrating the intermediate blood vessels 70m and the deep blood vessel image 96d illustrating the deep blood vessels 70d are intermediately highlighted is generated as the display image 98 by combining the primary intermediate emphasis image signals of the intermediate layer and of the deep layer, and the primary image signal that is a non-emphasis image signal of the surface.

The emphasis mode M12 (intermediate blood vessel emphasis-superficial and deep blood vessel intermediate emphasis mode) is a mode of highlighting the blood vessels located in the intermediate layer of the observation object O and to intermediately emphasize the blood vessels located in the deep layer. In the emphasis mode M12, in the case where the imager 22 is a monochrome imager, the laser light source 46-1 (laser 1) that is the emphasis narrowband light source for the superficial blood vessels, the laser light source 46-2

(laser 2) that is the non-emphasis narrowband light source for the superficial blood vessel, the laser light source 46-3 (laser 3) that is the emphasis narrowband light source for the intermediate blood vessels, the laser light source 46-5 (laser 5) that is the emphasis narrowband light source for the deep blood vessels, and the laser light source 46-6 (laser 6) that is the non-emphasis narrowband light source for the deep blood vessels are turned on in order in the same radiation cycle. Then, a primary intermediate emphasis image signal of the surface is generated by weighting and averaging the primary image signal that is an emphasis image signal of the surface and the primary image signal that is a non-emphasis image signal of the surface, and a primary intermediate emphasis image signal of the deep layer is generated by weighting and averaging the primary image signal that is an emphasis image signal of the deep layer and the primary image signal that is a non-emphasis image signal of the deep layer, and an intermediate emphasis image in which the intermediate blood vessel image 96m illustrating the intermediate blood vessels 70m is highlighted, and the superficial blood vessel image 96s illustrating the superficial blood vessels 70s and the deep blood vessel image 96d illustrating the deep blood vessels 70d are intermediately highlighted is generated as the display image 98 by combining the primary intermediate emphasis image signals of the surface and of the deep layer, and the primary image signal that is an emphasis image signal of the intermediate layer.

The emphasis mode M13 (superficial and deep blood vessel intermediate emphasis mode) is a mode of intermediately emphasizing the blood vessels located in the surface of the observation object O and to intermediately emphasize the blood vessels located in the deep layer. In the emphasis mode M13, in the case where the imager 22 is a monochrome imager, the laser light source 46-1 (laser 1) that is the emphasis narrowband light source for the superficial blood vessels, the laser light source 46-2 (laser 2) that is the non-emphasis narrowband light source for the superficial blood vessel, the laser light source 46-4 (laser 4) that is the non-emphasis narrowband light source for the intermediate blood vessels, the laser light source 46-5 (laser 5) that is the emphasis narrowband light source for the deep blood vessels, and the laser light source 46-6 (laser 6) that is the non-emphasis narrowband light source for the deep blood vessels are turned on in order in the same radiation cycle. Then, a primary intermediate emphasis image signal of the surface is generated by weighting and averaging the primary image signal that is an emphasis image signal of the surface and the primary image signal that is a non-emphasis image signal of the surface, and a primary intermediate emphasis image signal of the deep layer is generated by weighting and averaging the primary image signal that is an emphasis image signal of the deep layer and the primary image signal that is a non-emphasis image signal of the deep layer, and an intermediate emphasis image in which the superficial blood vessel image 96s illustrating the superficial blood vessels 70s and the deep blood vessel image 96d illustrating the deep blood vessels 70d are intermediately highlighted is generated as the display image 98 by combining the primary intermediate emphasis image signals of the surface and of the deep layer, and the primary image signal that is a non-emphasis image signal of the intermediate surface.

The emphasis mode M14 (deep blood vessel emphasis-superficial and intermediate blood vessel intermediate emphasis mode) is a mode of highlighting the blood vessels located in the deep layer of the observation object O, and to intermediately emphasize the blood vessels located in the surface and to intermediately emphasize the blood vessels in the intermediate layer. In the emphasis mode M14, in the case where the imager 22 is a monochrome imager, the laser light source 46-1 (laser 1) that is the emphasis narrowband light source for the superficial blood vessels, the laser light source 46-2 (laser 2) that is the non-emphasis narrowband light source for the superficial blood vessel, the laser light source 46-3 (laser 3) that is the emphasis narrowband light source for the intermediate blood vessels, the laser light source 46-4 (laser 4) that is the non-emphasis narrowband light source for the intermediate blood vessel, and the laser light source 46-5 (laser 5) that is the emphasis narrowband light source for the deep blood vessels are turned on in order in the radiation cycle. Then, a primary intermediate emphasis image signal of the surface is generated by weighting and averaging the primary image signal that is an emphasis image signal of the surface and the primary image signal that is a non-emphasis image signal of the surface, and a primary intermediate emphasis image signal of the intermediate layer is generated by weighting and averaging the primary image signal that is an emphasis image signal of the intermediate layer and the primary image signal that is a non-emphasis image signal of the intermediate layer and an intermediate emphasis image in which the deep blood vessel image 96d illustrating the deep blood vessels 70d is highlighted, and the superficial blood vessel image 96s illustrating the superficial blood vessels 70s and the intermediate blood vessel image 96m illustrating the intermediate blood vessels 70m are intermediately highlighted is generated as the display image 98 by combining the primary intermediate emphasis image signals of the surface and of the intermediate layer, and the primary image signal that is an emphasis image signal of the deep layer.

The emphasis mode M15 (superficial and intermediate blood vessel intermediate emphasis mode) is a mode of intermediately emphasizing the blood vessels located in the surface of the observation object O and to intermediately emphasize the blood vessels located in the intermediate layer. In the emphasis mode M15, in the case where the imager 22 is a monochrome imager, the laser light source 46-1 (laser 1) that is the emphasis narrowband light source for the superficial blood vessels, the laser light source 46-2 (laser 2) that is the non-emphasis narrowband light source for the superficial blood vessel, the laser light source 46-3 (laser 3) that is the emphasis narrowband light source for the intermediate blood vessels, the laser light source 46-4 (laser 4) that is the non-emphasis narrowband light source for the intermediate blood vessel, and the laser light source 46-6 (laser 6) that is the non-emphasis narrowband light source for the deep blood vessels are turned on in order in the radiation cycle. Then, a primary intermediate emphasis image signal of the surface is generated by weighting and averaging the primary image signal that is an emphasis image signal of the surface and the primary image signal that is a non-emphasis image signal of the surface, and a primary intermediate emphasis image signal of the intermediate layer is generated by weighting and averaging the primary image signal that is an emphasis image signal of the intermediate layer and the primary image signal that is a non-emphasis image signal of the intermediate layer, and an intermediate emphasis image in which the superficial blood vessel image 96s illustrating the superficial blood vessels 70s and the intermediate blood vessel image 96m illustrating the intermediate blood vessels 70m are intermediately highlighted is generated as the display image 98 by combining the primary intermediate emphasis image signals of the surface and of the intermediate layer, and the primary image signal that is a non-emphasis image signal of the deep surface.

Then, the emphasis mode M16 (superficial, intermediate, and deep blood vessel intermediate emphasis mode) is a mode of intermediately emphasizing the blood vessels in the surface of the observation object O, to intermediately emphasize the blood vessels in the intermediate layer, and to intermediately emphasize the blood vessels in the deep layer. In the emphasis mode M16, in the case where the imager 22 is a monochrome imager, the laser light source 46-1 (laser 1) that is the emphasis narrowband light source for the superficial blood vessels, the laser light source 46-2 (laser 2) that is the non-emphasis narrowband light source for the superficial blood vessel, the laser light source 46-3 (laser 3) that is the emphasis narrowband light source for the intermediate blood vessels, the laser light source 46-4 (laser 4) that is the non-emphasis narrowband light source for the intermediate blood vessel, the laser light source 46-5 (laser 5) that is the emphasis narrowband light source for the deep blood vessels, and the laser light source 46-6 (laser 6) that is the non-emphasis narrowband light source for the deep blood vessels are turned on in order in the radiation cycle. Then, a primary intermediate emphasis image signal of the surface is generated by weighting and averaging the primary image signal that is an emphasis image signal of the surface and the primary image signal that is a non-emphasis image signal of the surface, a primary intermediate emphasis image signal of the intermediate layer is generated by weighting and averaging the primary image signal that is an emphasis image signal of the intermediate layer and the primary image signal that is a non-emphasis image signal of the intermediate layer, and a primary intermediate emphasis image signal of the deep layer is generated by weighting and averaging the primary image signal that is an emphasis image signal of the deep layer and the primary image signal that is a non-emphasis image signal of the deep layer, and an intermediate emphasis image in which all of the superficial blood vessel image 96s illustrating the superficial blood vessels 70s, the intermediate blood vessel image 96m illustrating the intermediate blood vessels 70m, and the deep blood vessel image 96d illustrating the deep blood vessels 70d are intermediately highlighted is generated as the display image 98 by combining the primary intermediate emphasis image signals of the surface, of the intermediate layer, and of the deep layer.

Note that, in the case where the imager 22 is a monochrome imager, it has been described that only the laser light sources used in the selected emphasis mode are turned on in order in the same radiation cycle as illustrated in FIGS. 9 and 12. However, as illustrated in FIG. 17, all of the laser light sources 46-1 to 46-6 may be turned on in order in the same radiation cycle regardless of the emphasis mode. In this case, the primary image signal is acquired for each lighted laser light source and is stored in the primary image memory 84. Then, the image selector 86 sends only the necessary primary image signal from among the primary image signals stored in the primary image memory 84 to the primary intermediate emphasis image generator 90 and the display image generator 92 according to the selected emphasis mode. As a result, the primary intermediate emphasis image generator 90 and the display image generator 92 can execute the above-described processing.

Further, in the case of using a color imager having BGR color filters as the imager 22, for example, a lighting method of alternately repeating lighting of the laser light source 46-1 (laser 1), the laser light source 46-3 (laser 3), and the laser light source 46-5 (laser 5), and lighting of the laser light source 46-2 (laser 2), the laser light source 46-4 (laser 4), and the laser light source 46-6 (laser 6) as one radiation cycle may be employed. In this case, an equivalent image synthesis processing can be performed by acquiring the primary image signal that is the emphasis image signal of the surface in the B light detection element, the primary image signal that is the emphasis image signal of the intermediate layer in the G light detection element, and the primary image signal that is an emphasis image signal of the deep layer in the R light detection element at the time of lighting the laser light source 46-1 (laser 1), the laser light source 46-3 (laser 3), and the laser light source 46-5 (laser 5), and acquiring the primary image signal that is the non-emphasis image signal of the surface in the B light detection element, the primary image signal that is a non-emphasis image signal of the intermediate layer in the G light detection element, and the primary image signal that is a non-emphasis image signal of the intermediate layer in the R light detection element at the time of lighting the laser light source 46-2 (laser 2), the laser light source 46-4 (laser 4), and the laser light source 46-6 (laser 6), and storing the primary image signals to the primary image memory 84.

Note that the above example has been described as the combinations for reproduction of white. However, in the case where no reproduction of white is necessary depending on the purpose of use, arbitrary color image signals may be combined and displayed by using only a combination of the B image signal and the G image signal, instead of using all of the BGR color image signals.

Further, in the case where no reproduction of white is necessary, the primary intermediate emphasis image signal may be generated in combination of an emphasis image signal and a non-emphasis image signal in different color ranges instead of in the same color range. For example, in the case of acquiring a monochrome image signal, an intermediate emphasis image in which the degree of emphasis is similarly adjusted can be generated by a combination of image signals having different degrees of emphasis to an arbitrary diagnosis target substance.

Further, in the present embodiment, a laser light source has been used as the narrowband light source. However, an LED can be used. To widen the adjustable range of contrast, a laser light source capable of providing a contrast difference between an emphasis image signal and a non-emphasis image signal in a narrower band is favorable. However, a similar effect can be obtained with an LED.

Figure 18:
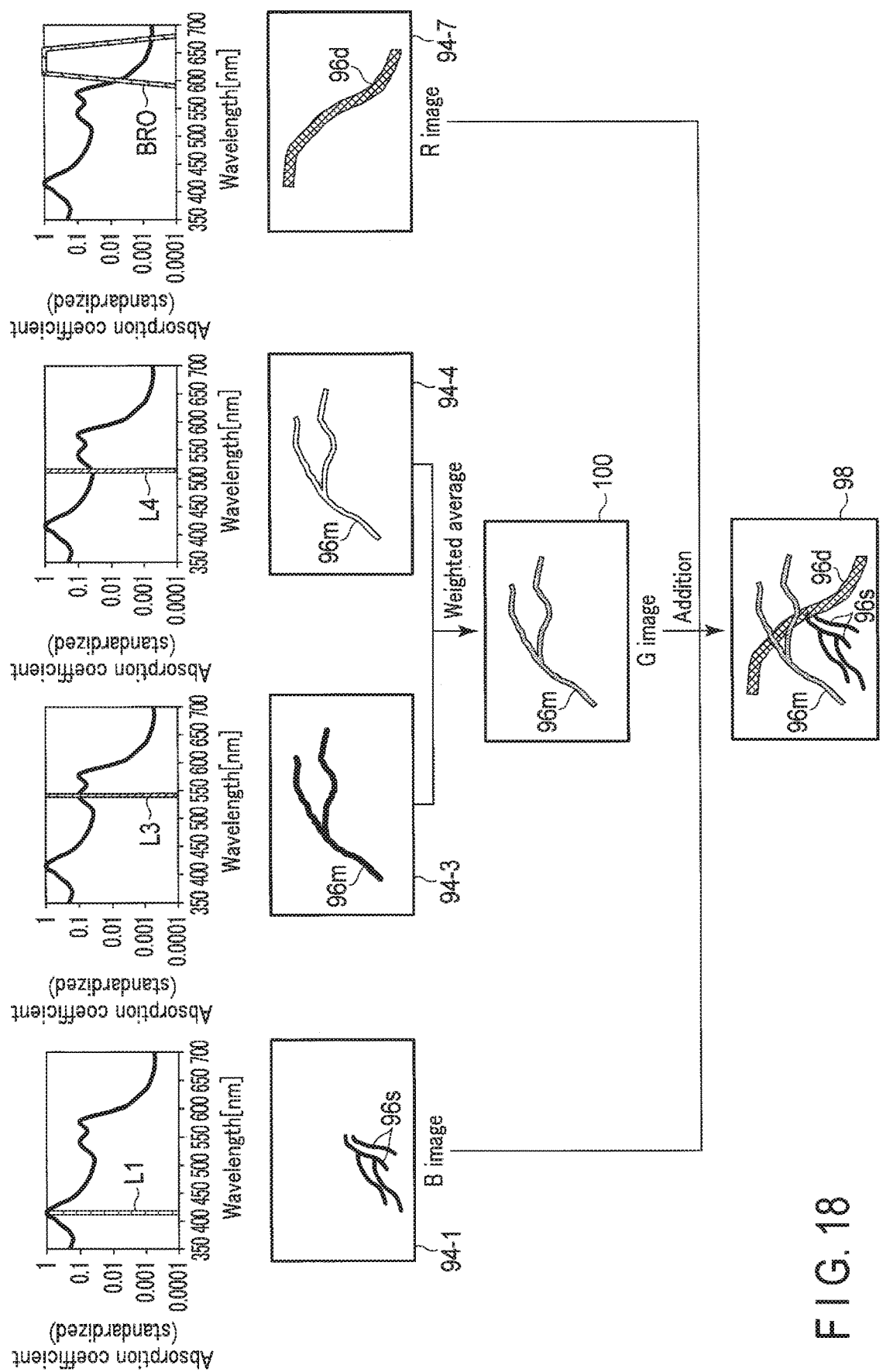
FIG. 18 is a diagram schematically illustrating a flow of display image generation in a superficial blood vessel emphasis-intermediate blood vessel intermediate emphasis mode in an endoscope apparatus according to a modification.

Note that, in the present embodiment, the primary image signals have been acquired with narrowband light for all the depths of the surface, the intermediate layer, and the deep layer (all the color ranges of the blue range 60B, the green range 60G, and the red range 60R). However, the primary image signal may be acquired with a broad band light having a broad wavelength range for the layer that does not require the emphasis or intermediate emphasis. FIG. 18 illustrates image synthesis images of an example in which the surface is emphasized, the intermediate layer is intermediately emphasized, and the broadband light BRO is used for the deep layer.

As compared with the example of the above-described emphasis mode M4 (superficial blood vessel emphasis-intermediate blood vessel intermediate emphasis mode) illustrated in FIG. 13, a primary image signal 94-7, which is acquired with the broadband light BRO having a wideband wavelength of the red range 60R, is used for generation of a display image as the red (R) image signal, in place of the primary image signal 94-6 that is a deep layer non-emphasis image signal by the laser light source 46-6 (laser 6). The primary image signal 94-7 becomes an intermediate emphasis image signal of the deep layer, but the display image 98 becomes an intermediate emphasis image in which the superficial blood vessels 70s are emphasized and the intermediate blood vessels 70m and the deep blood vessels 70d are intermediately emphasized. However, the degree of emphasis cannot be adjusted in the deep layer. In the case of an image with only narrowband light, color reproduction is difficult due to lack of the wavelength for the white light source. However, the color reproducibility can be easily improved by use of the broadband light BRO.

As the broadband light BRO, light from an LED light source or light obtained by cutting out a specific wavelength range from a white light source such as a xenon lamp by a filter can be used.

Note that, in the above-described embodiment, the endoscope apparatus 10 has the sixteen emphasis modes M1 to M16. However, it is not indispensable to have all the emphasis modes.

Further, the endoscope apparatus 10 may also have another emphasis mode. The endoscope apparatus 10 may have a mode of radiating normal light having different color tones, an another special light emphasis mode of highlighting a specific target substance in the observation object O, a fluorescent light emphasis mode of observing fluorescent light generated when excited light is radiated on the observation object O or a pharmacological agent, and or the like.

Further, in the above-described embodiment, the diagnosis target substance has been oxyhemoglobin, but the diagnosis target substance may be another substance. For example, the diagnosis target substance may be reduced hemoglobin. Further, the diagnosis target substance may be blood in which the oxyhemoglobin and the reduced hemoglobin are mixed. In that case, the absorption spectrum is obtained by multiplying a mixture ratio of the absorption spectrum of the oxyhemoglobin and the absorption spectrum of the reduced hemoglobin.

Further, the diagnosis target substance may be a known autofluorescent substance, a fluorescent pharmacological agent, or a substance contained in a living body, such as the fat, bilirubin or sugar, other than hemoglobin.

As described above, the endoscope apparatus 10 according to an embodiment of the present invention includes the imager 22 configured to detect the reflected and scattered light RL of the illumination light IL radiated to the observation object O and output the imaging signal, the image processor 24 configured to generate the display image from the imaging signal, and the image display 16 configured to display the generated display image. Here, the image processor 24 includes the intermediate emphasis image generator 88. The intermediate emphasis image generator 88 generates an intermediate emphasis image that is an image in which the degree of emphasis of the diagnosis target substance is intermediate with respect to an emphasis image that is an image generated from emphasis image signals and a non-emphasis image that is an image generated from non-emphasis image signals, based on the emphasis image signals that are imaging signals for the reflected and scattered light of the illumination light including rays of emphasis narrowband light that is light in emphasis wavelength ranges that allows the diagnosis target substance existing in the observation object O to be emphasized and observed, and the non-emphasis image signals that are imaging signals for the reflected and scattered light of the illumination light including non-emphasis narrowband light that is light in non-emphasis wavelength ranges not including the emphasis wavelength ranges.

The emphasis image generated with the light including an emphasis wavelength and the non-emphasis image generated with the light not including the emphasis wavelength are synthesized, and the intermediate emphasis image is generated, whereby the degree of emphasis of the diagnosis target substance in the depth region emphasized by the emphasis narrowband light can be adjusted. Therefore, the degree of emphasis of the diagnosis target substance in each specific depth region can be adjusted.

Further, the endoscope apparatus 10 according to an embodiment of the present invention can further include a plurality of narrowband light sources configured to emit illumination light including rays of narrowband light different from one another. Here, the plurality of narrowband light sources includes at least a first emphasis narrowband light source configured to emit first emphasis narrowband light with a peak wavelength or a central wavelength included in one of the plurality of emphasis wavelength ranges, and a first non-emphasis narrowband light source configured to emit first non-emphasis narrowband light with a peak wavelength or a central wavelength included in one of the non-emphasis wavelength ranges. In this case, the imager 22 acquires a first emphasis image signal that is an imaging signal for the reflected and scattered light including the first emphasis narrowband light, and a first non-emphasis image signal that is an imaging signal for the reflected and scattered light including the first non-emphasis narrowband light, as the first and second primary image signals (for example, the primary image signals 94-3 and 94-4). Then, the intermediate emphasis image generator 88 synthesizes the first primary image signal and the second primary image signal to generate the first primary intermediate emphasis image signal 100.

The first emphasis image signal by the light including the first emphasis narrowband light and the first non-emphasis image by the light including the first non-emphasis narrowband light are synthesized to generate the first primary intermediate emphasis image signal 100, whereby the first primary intermediate emphasis image signal 100 in which the degree of emphasis of the diagnosis target substance in the depth region emphasized by the first emphasis narrowband light is adjusted to an intermediate degree of emphasis can be generated.

Further, the plurality of narrowband light sources can further include at least one of the second emphasis narrowband light source configured to emit the second emphasis narrowband light different from the first emphasis narrowband light, and the second non-emphasis narrowband light source configured to emit the second non-emphasis narrowband light different from the first non-emphasis narrowband light. In this case, the imager 22 further acquires at least one of a second emphasis image signal that is an imaging signal for the reflected and scattered light including the second emphasis narrowband light, and a second non-emphasis image signal that is an imaging signal for the reflected and scattered light including the second non-emphasis narrowband light, as a third primary image signal (for example, the primary image signal 94-1), and the intermediate emphasis image generator 88 generates an intermediate emphasis image based on the first primary intermediate emphasis image signal 100 and the third primary image signal.

The intermediate emphasis image can be generated by acquiring either the second emphasis image signal or the second non-emphasis image signal, and synthesizing the acquired image signal to the first primary intermediate emphasis image signal 100 in this manner.

Further, the plurality of narrowband light sources can further include at least one of the third emphasis narrowband light source configured to emit the third emphasis narrowband light different from the first and second emphasis narrowband light, and the third non-emphasis narrowband light source configured to emit the third non-emphasis narrowband light different from the first and second non-emphasis narrowband light. In this case, the imager 22 further acquires at least one of a third emphasis image signal generated based on the reflected and scattered light including the third emphasis narrowband light, and a third non-emphasis image signal generated based on the reflected and scattered light including the third non-emphasis narrowband light, as a fourth primary image signal (for example, the primary image signal 94-6), and the intermediate emphasis image generator generates an intermediate emphasis image based on the first primary intermediate emphasis image signal 100, the third primary image signal, and the fourth primary image signal.

The intermediate emphasis image can be generated by synthesizing the first primary intermediate emphasis image signal 100, either the second emphasis image signal or the second non-emphasis image signal, and either the third emphasis image signal or the third non-emphasis image signal in this manner.

Alternatively, the plurality of narrowband light sources may further include the second emphasis narrowband light source configured to emit the second emphasis narrowband light different from the first emphasis narrowband light, and the second non-emphasis narrowband light source configured to emit the second non-emphasis narrowband light different from the first non-emphasis narrowband light, in addition to the first emphasis narrowband light source and the first non-emphasis narrowband light source. In this case, the imager 22 further acquires a second emphasis image signal generated based on the reflected and scattered light including the second emphasis narrowband light, and a second non-emphasis image signal generated based on the reflected and scattered light including the second non-emphasis narrowband light, as third and fourth primary image signals, and the intermediate emphasis image generator 88 synthesizes the third primary image signal and the fourth primary image signal to generate a second primary intermediate emphasis image signal, and generates an intermediate emphasis image based on the first primary intermediate emphasis image signal and the second primary intermediate emphasis image signal.

The intermediate emphasis image can be generated by generating the second intermediate emphasis image signal, and synthesizing the first intermediate emphasis image signal and the second intermediate emphasis image signal in this manner.

In this case, the plurality of narrowband light sources further includes at least one of the third emphasis narrowband light source configured to emit the third emphasis narrowband light different from the first and second emphasis narrowband light, and the third non-emphasis narrowband light source configured to emit the third non-emphasis narrowband light different from the first and second non-emphasis narrowband light. Then, the imager 22 further acquires at least one of a third emphasis image signal generated based on the reflected and scattered light including the third emphasis narrowband light, and a third non-emphasis image signal generated based on the reflected and scattered light including the third non-emphasis narrowband light, as a fifth primary image signal, and the intermediate emphasis image generator 88 generates an intermediate emphasis image based on the first primary intermediate emphasis image signal, the second primary intermediate emphasis image signal, and the fifth primary image signal.

The intermediate emphasis image can be generated by synthesizing either the third emphasis image signal or the third non-emphasis image signal in addition to the first intermediate emphasis image signal and the second intermediate emphasis image signal in this manner.

Alternatively, the plurality of narrowband light sources may further include the third emphasis narrowband light source configured to emit the third emphasis narrowband light different from the first and second emphasis narrowband light, and the third non-emphasis narrowband light source configured to emit the third non-emphasis narrowband light different from the first and second non-emphasis narrowband light. In this case, the imager 22 further acquires a third emphasis image signal generated based on the reflected and scattered light including the third emphasis narrowband light, and a third non-emphasis image signal generated based on the reflected and scattered light including the third non-emphasis narrowband light, as fifth and sixth primary image signals, and the intermediate emphasis image generator 88 synthesizes the fifth primary image signal and the sixth primary image signal to generate a third primary intermediate emphasis image signal, and generates an intermediate emphasis image based on the first primary intermediate emphasis image signal, the second primary intermediate emphasis image signal, and the third primary intermediate emphasis image signal.

The intermediate emphasis image may be generated by synthesizing the first intermediate emphasis image signal, the second intermediate emphasis image signal, and the third intermediate emphasis image signal in this manner.

Note that, here, the first emphasis narrowband light and the first non-emphasis narrowband light have the reach length up to the first depth region, and the first depth region is one of three depth regions of the superficial region 72s, the intermediate region 72m, and the deep region 72d, with respect to the observation object O.

As described above, the first emphasis narrowband light and the first non-emphasis narrowband light have the reach length up to the first depth region, and thus the degree of emphasis of the diagnosis target substance in the first depth region with respect to the observation object O can be changed.

Further, the first emphasis narrowband light and the first non-emphasis narrowband light have the reach length up to the first depth region, and the second emphasis narrowband light and the second non-emphasis narrowband light have the reach length up to a second depth region. The first depth region is one of the three depth regions of the superficial region 72s, the intermediate region 72m, and the deep region 72d with respect to the observation object O, and the second depth region is any of the three depth regions that is different from the first depth region.

As described above, the second emphasis narrowband light and the second non-emphasis narrowband light have the reach length up to the second depth region different from the first depth region, and thus the relative degree of emphasis of the diagnosis target substance in the first depth region to the diagnosis target substance in the second depth region can be changed.

Alternatively, the first emphasis narrowband light and the first non-emphasis narrowband light have the reach length up to the first depth region, the second emphasis narrowband light and the second non-emphasis narrowband light have the reach length up to the second depth region, and the third emphasis narrowband light and the third non-emphasis narrowband light have the reach length up to a third depth region. The first depth region is one of the three depth regions of the superficial region, the intermediate region, and the deep region with respect to the observation object O, the second depth region is any of the three depth regions that is different from the first depth region, and the third depth region is one of the three depth regions that is different from the first depth region and the second depth region.

As described above, the third emphasis narrowband light and the third non-emphasis narrowband light have the reach length up to the third depth region different from the first and second depth regions, and thus the relative degree of emphasis of the diagnosis target substance in the first depth region to the diagnosis target substance in the second and third depth regions can be changed.

In this case, the narrowband light having the reach length up to the superficial region 72s is included in the blue range 60B, the narrowband light having the reach length up to the intermediate region 72m is included in the green range 60G, and the narrowband light having the reach length up to the deep region 72d is included in the red range 60R, of the rays of narrowband light.

As can be seen, the depth region and the color range have a correlation.

Further, in the case where the first emphasis narrowband light and the first non-emphasis narrowband light have the reach length up to the first depth region, the second emphasis narrowband light and the second non-emphasis narrowband light have the reach length up to the second depth region, and the third emphasis narrowband light and the third non-emphasis narrowband light have the reach length up to a third depth region, the first depth region is one of the three depth regions of the superficial region 72s, the intermediate region 72m, and the deep region 72d with respect to the observation object O, the second depth region is any of the three depth regions that is different from the first depth region, and the third depth region is one of the three depth regions that is different from the first depth region and the second depth region, and the narrowband light having the reach length up to the superficial region 72s is included in the blue range 60B, the narrowband light having the reach length up to the intermediate region 72m is included in the green range 60G, and the narrowband light having the reach length up to the deep region 72d is included in the red range 60R, of the rays of narrowband light, the first primary intermediate emphasis image signal, the second primary intermediate emphasis image signal, and the third primary intermediate emphasis image signal are combined at a luminance ratio where white is reproducible.

The first primary intermediate emphasis image, the second primary intermediate emphasis image, and the third primary intermediate emphasis image are synthesized at the luminance ratio where white is reproduced, whereby the intermediate emphasis image that is the display image 98 can be displayed as a so-called color image based on white illumination.

Further, each of the emphasis wavelength ranges is a wavelength range including at least one of the maximum wavelength that takes the maximum values 62B and 62G with respect to the optical absorption spectrum of the diagnosis target substance existing in the observation object O, and the color-range largest wavelength that takes the color-range largest values that are the largest values 64B, 64G, and 64R in any of the three color ranges of the blue range 60B, the green range 60G, and the red range 60R.

As described above, the emphasis wavelength range can include at least one of the wavelength that takes the maximum value and the wavelength that takes the largest value in each color range.

Further, each of the non-emphasis wavelength ranges includes at least one of the minimum wavelength that takes the minimum values 66B and 66G with respect to the optical absorption spectrum of the diagnosis target substance existing in the observation object O, and the color-range smallest wavelength that takes the color-range smallest values that are the smallest values 68B, 68G, and 68R in any of the three color ranges of the blue range 60B, the green range 60G, and the red range 60R.

As described above, the non-emphasis wavelength range can include at least one of the wavelength that takes the minimum value and the wavelength that takes the smallest value in each color range.

Note that each of the non-emphasis wavelength ranges is a color range where the minimum value or the color-range smallest value exists, and is a wavelength range having a value equal to or less than 1.5 times of at least one of the minimum value and the color-range smallest value.

As described above, when the non-emphasis wavelength range is a wavelength range having a value equal to or less than 1.5 times of the minimum value or the smallest value in each color range, the light absorption is small and thus it is favorable.

Further, the observation object O is a living tissue, and the diagnosis target substance is hemoglobin included in the observation object O.

Therefore, the blood vessels in the living tissues can be emphasized.

Note that each of the narrowband light sources includes a laser light source.

As described above, the plurality of narrowband light sources can be configured by laser light sources.

Alternatively, each of the narrowband light sources may include an LED light source.

As described above, the plurality of narrowband light sources can be configured by LED light sources.

Further, a broadband light source configured to emit the broadband light BRO may be further provided. The broadband light BRO has a broader wavelength width than the rays of emphasis narrowband light and the rays of non-emphasis narrowband light, and has a different peak wavelength from the emphasis wavelength ranges and the non-emphasis wavelength ranges, or can be emitted by differentiating the peak wavelength from the emphasis wavelength ranges and the non-emphasis wavelength ranges by cutting or attenuating components of the wavelengths of the emphasis wavelength ranges and the non-emphasis wavelength ranges. In this case, the intermediate emphasis image generator 88 generates an intermediate emphasis image, using a broadband light image signal that is an imaging signal for the reflected and scattered light of the broadband light BRO emitted from the broadband light source, as at least one of the emphasis image signals and the non-emphasis image signals.

The intermediate emphasis image can be generated even in the case where the broadband light source is included and an image by the broadband light BRO is combined.

Further, the endoscope apparatus 10 according to an embodiment of the present invention can further include the primary image memory 84 configured to store at least one emphasis image signal and at least one non-emphasis image signal output from the imager 22, and the image selector 86 configured to select a combination of at least one desired emphasis image signal and at least one desired non-emphasis image signal. In this case, the intermediate emphasis image generator 88 reads the at least one emphasis image signal (for example, the primary image signal 94-3) and the at least one non-emphasis image signal (for example, the primary image signal 94-4) selected by the image selector 86 from the primary image memory 84, and generates the primary intermediate emphasis image signal 100 by performing predetermined synthesis processing.

Necessity of definition of the order of acquisition of the emphasis image signal and the non-emphasis image signal can be eliminated by including the primary image memory 84 and the image selector 86.

Here, the primary image memory 84 stores emphasis image signals and non-emphasis image signals, and the image selector 86 selects at least one set of one emphasis image signal and one non-emphasis image signal based on a predetermined condition including at least one of the depth region, the color range, and the acquisition timing, from the emphasis image signals and the non-emphasis image signals. Then, the intermediate emphasis image generator 88 reads the at least one set of one emphasis image signal and one non-emphasis image signal selected by the image selector 86 from the primary image memory 84, and generates at least one primary intermediate emphasis image signal 100 by performing predetermined synthesis processing.

As described above, the primary intermediate emphasis image signal 100 can be generated by selecting the signals from the emphasis image signals and the non-emphasis image signals.

In this case, the imager 22 irradiates the at least one set of one emphasis image signal and one non-emphasis image signal selected by the image selector 86 with a pattern having a time-divided fixed radiation cycle to acquires the at least one set of one emphasis image signal and one non-emphasis image signal selected by the image selector 86 at a fixed cycle, and the primary image memory 84 stores the acquired at least one set of one emphasis image signal and one non-emphasis image signal. Then, the intermediate emphasis image generator 88 reads the at least one set of one emphasis image signal and one non-emphasis image signal stored in the primary image memory 84, and generates at least one primary intermediate emphasis image signal 100 by performing predetermined synthesis processing.

As described above, the primary intermediate emphasis image signal 100 can be generated by acquiring only the selected emphasis image signal and non-emphasis image signal.

Alternatively, the imager 22 irradiates the rays of emphasis narrowband light and the rays of non-emphasis narrowband light with a pattern having a time-divided fixed radiation cycle to acquire the emphasis image signals and the non-emphasis image signals at a fixed cycle, and the primary image memory 84 stores the acquired emphasis image signals and the non-emphasis image signals. Then, the image selector 86 selects at least one set of one emphasis image signal and one non-emphasis image signal in the same depth region or in the same color range within the same radiation cycle, and the intermediate emphasis image generator 88 reads the at least one set of one emphasis image signal and one non-emphasis image signal selected by the image selector 86 from the primary image memory 84, and generates at least one primary intermediate emphasis image signal by performing predetermined synthesis processing.

As described above, the primary intermediate emphasis image signal 100 can be generated by acquiring all the emphasis image signals and the non-emphasis image signals and selectively using the signals.

In this case, the image selector 86 can select two or more sets of one emphasis image signal and one non-emphasis image signal based on a predetermine condition from the emphasis image signals and the non-emphasis image signals, and the intermediate emphasis image generator 88 can generate two or more primary intermediate emphasis image signals and generate an intermediate emphasis image based on the generated primary intermediate emphasis image signals.

As described above, the intermediate emphasis image can be generated from two or more sets of emphasis image signals and non-emphasis image signals.

Note that the image selector 86 selects at least one primary intermediate emphasis image signal, at least one emphasis image signal, and non-emphasis image signals in different color ranges so as to generate an image based on white illumination according to a combination.

A so-called color image based on white illumination can be obtained by combining the image signals in different color ranges.

The endoscope apparatus 10 according to an embodiment of the present invention may further include the input device 18 configured to input one emphasis mode from among the emphasis modes, the emphasis mode storage 78 configured to store a drive pattern of the light sources, selected images, and an image synthesis method for each of the emphasis modes, and the image setting unit 82 that is a controller configured to read the drive pattern of the light sources, the selected images, and the image synthesis method from the emphasis mode storage 78 according to the emphasis mode input to the input device 18 and control the image processor 24 according to the read information to cause the image processor 24 to generate the intermediate emphasis image.

As described above, the user can input the emphasis mode and can perform control based on the emphasis mode.

In this case, the emphasis mode includes a first emphasis mode to display a first intermediate emphasis image that is an intermediate emphasis image of a diagnosis target substance at least in a specific depth region, and a second emphasis mode to display a second intermediate emphasis image that is an intermediate emphasis image for a diagnosis target substance in a depth region different from the first intermediate emphasis image.

As described above, the intermediate emphasis image according to the input emphasis mode can be generated and displayed.

The present invention has been described based on an embodiment but is in no way limited to the embodiments described above. Needless to say, the present invention can be modified in various manners, without departing from the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
an imager configured to detect reflected and scattered light of illumination light radiated to an observation object and generate an imaging signal of an image based on the reflected and scattered light detected, the illumination light including light in three wavelength ranges corresponding to first, second, and third depth regions different from each other; and
an image processor configured to:
receive:
a first emphasis image signal of a first emphasis image generated by the imager based on emphasis narrowband light included in an emphasis wavelength range that emphasizes a diagnosis target substance existing in the observation object;

a first non-emphasis image signal of a first non-emphasis image generated by the imager based on non-emphasis narrowband light included in a non-emphasis wavelength range not including the emphasis wavelength range; and
other image signals of other images generated by the imager, the other image signals corresponding to all wavelength ranges not including the emphasis wavelength range and the non-emphasis wavelength range, in the three wavelength ranges;
generate a first primary intermediate emphasis image signal of a first primary intermediate emphasis image in which a degree of emphasis of the diagnosis target substance is between emphasis of the diagnosis target substance in the first emphasis image and non-emphasis of the diagnostic target substance in the first non-emphasis image, based on the first emphasis image signal and the first non-emphasis image signal; and
generate a display image based on the first primary intermediate emphasis image signal and the other image signals.

2. The endoscope apparatus according to claim 1, further comprising:
a plurality of narrowband light sources configured to emit the illumination light including rays of narrowband light different from one another,
wherein the plurality of narrowband light sources comprises:
a first emphasis narrowband light source configured to emit first emphasis narrowband light with a peak wavelength or a central wavelength included in the emphasis wavelength range; and
a first non-emphasis narrowband light source configured to emit first non-emphasis narrowband light with a peak wavelength or a central wavelength included in the non-emphasis wavelength range,
wherein the imager is configured to acquire:
the first emphasis image signal that is the imaging signal for the reflected and scattered light including the first emphasis narrowband light; and
the first non-emphasis image signal that is the imaging signal for the reflected and scattered light including the first non-emphasis narrowband light,
as first and second primary image signals, and
wherein the image processor is configured to synthesize the first primary image signal and the second primary image signal to generate the first primary intermediate emphasis image signal.

3. The endoscope apparatus according to claim 2,
wherein the plurality of narrowband light sources further comprises at least one of:
a second emphasis narrowband light source configured to emit second emphasis narrowband light different from the first emphasis narrowband light; and
a second non-emphasis narrowband light source configured to emit second non-emphasis narrowband light different from the first non-emphasis narrowband light,
wherein the imager is configured to acquire further at least one of:
a second emphasis image signal that is the imaging signal for the reflected and scattered light including the second emphasis narrowband light; and
a second non-emphasis image signal that is the imaging signal for the reflected and scattered light including the second non-emphasis narrowband light,
as a third primary image signal, and
wherein the image processor is configured to generate the intermediate emphasis image based on the first primary intermediate emphasis image signal and the third primary image signal.

4. The endoscope apparatus according to claim 3,
wherein the plurality of narrowband light sources further comprises at least one of:
a third emphasis narrowband light source configured to emit third emphasis narrowband light different from the first emphasis narrowband light and the second emphasis narrowband light, and
a third non-emphasis narrowband light source configured to emit third non-emphasis narrowband light different from the first non-emphasis narrowband light and the second non-emphasis narrowband light,
wherein the imager is configured to generate at least one of:
a third emphasis image signal based on the reflected and scattered light including the third emphasis narrowband light, and
a third non-emphasis image signal based on the reflected and scattered light including the third non-emphasis narrowband light,
as a fourth primary image signal, and
wherein the image processor is configured to generate the display image based on the first primary intermediate emphasis image signal, the third primary image signal, and the fourth primary image signal.

5. The endoscope apparatus according to claim 4,
wherein each of the first emphasis narrowband light and the first non-emphasis narrowband light has a reach length up to the first depth region,
wherein each of the second emphasis narrowband light and the second non-emphasis narrowband light has a reach length up to the second depth region,
wherein each of the third emphasis narrowband light and the third non-emphasis narrowband light has a reach length up to the third depth region,
wherein the first depth region is one of three depth regions that are a superficial region, an intermediate region, and a deep region with respect to the observation object,
wherein the second depth region is one of the three depth regions, the one being different from the first depth region, and
wherein the third depth region is one of the three depth regions, the one being different from the first depth region and the second depth region.

6. The endoscope apparatus according to claim 5, wherein:
narrowband light having the reach length up to the superficial region is included in a blue range;
narrowband light having the reach length up to the intermediate region is included in a green range; and
narrowband light having the reach length up to the deep region is included in a red range,
of the rays of narrowband light.

7. The endoscope apparatus according to claim 3,
wherein each of the first emphasis narrowband light and the first non-emphasis narrowband light has a reach length up to the first depth region,
wherein each of the second emphasis narrowband light and the second non-emphasis narrowband light has a reach length up to the second depth region, wherein the first depth region is one of three depth regions that are a superficial region, an intermediate region, and a deep region with respect to the observation object, and wherein the second depth region is one of the three depth regions, the one being different from the first depth region.

8. The endoscope apparatus according to claim 2, wherein the plurality of narrowband light sources further comprises:
   a second emphasis narrowband light source configured to emit second emphasis narrowband light different from the first emphasis narrowband light; and
   a second non-emphasis narrowband light source configured to emit second non-emphasis narrowband light different from the first non-emphasis narrowband light,
wherein the imager is configured to generate:
   a second emphasis image signal based on the reflected and scattered light including the second emphasis narrowband light; and
   a second non-emphasis image signal based on the reflected and scattered light including the second non-emphasis narrowband light,
as a third primary image signal and a fourth primary image signal, and
wherein the image processor is configured to:
   synthesize the third primary image signal and the fourth primary image signal to generate a second primary intermediate emphasis image signal; and
   generate the display image based on the first primary intermediate emphasis image signal and the second primary intermediate emphasis image signal.

9. The endoscope apparatus according to claim 8, wherein the plurality of narrowband light sources further comprises:
   a third emphasis narrowband light source configured to emit third emphasis narrowband light different from the first emphasis narrowband light and the second emphasis narrowband light; and
   a third non-emphasis narrowband light source configured to emit third non-emphasis narrowband light different from the first non-emphasis narrowband light and the second non-emphasis narrowband light,
wherein the imager is configured to generate at least one of:
   a third emphasis image signal based on the reflected and scattered light including the third emphasis narrowband light; and
   a third non-emphasis image signal based on the reflected and scattered light including the third non-emphasis narrowband light,
as a fifth primary image signal, and
wherein the image processor is configured to generate the display image based on the first primary intermediate emphasis image signal, the second primary intermediate emphasis image signal, and the fifth primary image signal.

10. The endoscope apparatus according to claim 8, wherein the plurality of narrowband light sources further comprises:
    a third emphasis narrowband light source configured to emit third emphasis narrowband light different from the first emphasis narrowband light and the second emphasis narrowband light; and
    a third non-emphasis narrowband light source configured to emit third non-emphasis narrowband light different from the first non-emphasis narrowband light and the second non-emphasis narrowband light,
wherein the imager is configured to generate:
    a third emphasis image signal based on the reflected and scattered light including the third emphasis narrowband light; and
    a third non-emphasis image signal based on the reflected and scattered light including the third non-emphasis narrowband light,
as a fifth primary image signal and a sixth primary image signal, and
wherein the image processor is configured to:
    synthesize the fifth primary image signal and the sixth primary image signal to generate a third primary intermediate emphasis image signal; and
    generate the display image based on the first primary intermediate emphasis image signal, the second primary intermediate emphasis image signal, and the third primary intermediate emphasis image signal.

11. The endoscope apparatus according to claim 10, wherein:
    each of the first emphasis narrowband light and the first non-emphasis narrowband light has a reach length up to the first depth region;
    each of the second emphasis narrowband light and the second non-emphasis narrowband light has a reach length up to the second depth region; and
    each of the third emphasis narrowband light and the third non-emphasis narrowband light has a reach length up to the third depth region,
wherein the first depth region is one of three depth regions that are a superficial region, an intermediate region, and a deep region with respect to the observation object,
wherein the second depth region is one of the three depth regions, the one being different from the first depth region,
wherein the third depth region is one of the three depth regions, the one being different from the first depth region and the second depth region,
wherein:
    narrowband light having a reach length up to the superficial region is included in a blue range;
    narrowband light having a reach length up to the intermediate region is included in a green range; and
    narrowband light having a reach length up to the deep region is included in a red range,
of the rays of narrowband light, and
    wherein the first primary intermediate emphasis image signal, the second primary intermediate emphasis image signal, and the third primary intermediate emphasis image signal are combined at a luminance ratio where white is reproducible.

12. The endoscope apparatus according to claim 2, wherein each of the first emphasis narrowband light and the first non-emphasis narrowband light has a reach length up to the first depth region, and
    wherein the first depth region is one of three depth regions that are a superficial region, an intermediate region, and a deep region with respect to the observation object.

13. The endoscope apparatus according to claim 1, wherein the emphasis wavelength range is a wavelength range including at least one of:
    a maximum wavelength that takes a maximum value with respect to an optical absorption spectrum of the diagnosis target substance existing in the observation object, and a color-range largest wavelength that takes a color-range largest value that is a largest value in a color range of three color ranges of a blue range, a green range, and a red range, or wherein the non-emphasis wavelength range includes at least one of:
a minimum wavelength that takes a minimum value with respect to an optical absorption spectrum of the diagnosis target substance existing in the observation object, and
a color-range smallest wavelength that takes a color-range smallest value that is a smallest value in a color range of three color ranges of a blue range, a green range, and a red range.

14. The endoscope apparatus according to claim 13, wherein the non-emphasis wavelength range is:
the color range in which the minimum value or the color-range smallest value exist; and
a wavelength range having a value equal to or less than 1.5 times of at least one of the minimum value and the color-range smallest value.

15. The endoscope apparatus according to claim 1, wherein the observation object is a living tissue, and
wherein the diagnosis target substance is hemoglobin included in the observation object.

16. The endoscope apparatus according to claim 1, further comprising:
a broadband light source configured to emit broadband light having a broader wavelength width than the emphasis narrowband light and the non-emphasis narrowband light, and having a different peak wavelength from peak wavelengths of the emphasis wavelength range and the non-emphasis wavelength range by cutting or attenuating components of wavelengths of the emphasis narrowband light and the non-emphasis narrowband light,
wherein the image processor is configured to generate the first primary intermediate emphasis image signal, using a broadband light image signal that is the imaging signal for the reflected and scattered light of the broadband light emitted from the broadband light source, as at least one of the first emphasis image signal and the first non-emphasis image signal.

17. The endoscope apparatus according to claim 1, further comprising:
a memory configured to store emphasis image signals and non-emphasis image signals generated by the imager,
wherein the image processor is configured to:
select the first emphasis image signal and the first non-emphasis image signal as a combination; and
read the first emphasis image signal and the first non-emphasis image signal selected from the memory; and
generate the first primary intermediate emphasis image signal by performing predetermined synthesis processing on the first emphasis image signal and the first non-emphasis image signal read from the memory.

18. The endoscope apparatus according to claim 17, wherein the image processor is configured to select the first emphasis image signal and the first non-emphasis image signal, as a set, based on a predetermined condition including at least one of a depth region, a color range, and acquisition timing, from the emphasis image signals and the non-emphasis image signals.

19. The endoscope apparatus according to claim 18, wherein:
the imager is configured to acquire the first emphasis image and the first non-emphasis image with a pattern having a time-divided fixed radiation cycle to generate the set of the first emphasis image signal and the first non-emphasis image signal selected by the image processor at a fixed cycle;
the memory is configured to store the set of the first emphasis image signal and the first non-emphasis image signal generated; and
the image processor is configured to read the set of the first emphasis image signal and the first non-emphasis image signal stored in the memory, and generate the first primary intermediate emphasis image signal by performing predetermined synthesis processing, or wherein:
the imager is configured to detect rays of the emphasis narrowband light and rays of the non-emphasis narrowband light with a pattern having a time-divided fixed radiation cycle to generate the first emphasis image signal and the first non-emphasis image signal at a fixed cycle;
the memory is configured to store the first emphasis image signal and the first non-emphasis image signal generated; and
the image processor is configured to:
select the set of the first emphasis image signal and the first non-emphasis image signal being in a same depth region or in a same color range, in the same radiation cycle;
read the set of the first emphasis image signal and the first non-emphasis image signal selected from the memory; and
generate the first primary intermediate emphasis image signal by performing predetermined synthesis processing on the first emphasis image signal and the first non-emphasis image signal read from the memory.

20. The endoscope apparatus according to claim 18, wherein the image processor is configured to:
select two or more sets of the first emphasis image signal and the first non-emphasis image signal based on the predetermined condition, from the emphasis image signals and the non-emphasis image signals; and
generate two or more of the first primary intermediate emphasis image signal based on the two or more sets of the first emphasis image signal and the first non-emphasis image signal.

21. The endoscope apparatus according to claim 18, wherein the image processor is configured to:
select the first primary intermediate emphasis image signal, the first emphasis image signal, and the first non-emphasis image signal in different color ranges; and
generate an image based on white illumination based on a combination of the first primary intermediate emphasis image signal, the first emphasis image signal, and the first non-emphasis image signal selected.

22. The endoscope apparatus according to claim 1, further comprising:
a controller configured to:
receive input of an emphasis mode from among a plurality of emphasis modes;

control an emphasis mode storage to store a drive pattern of a light source, a selected image, an image synthesis method for each of the plurality of emphasis modes;

read the drive pattern of the light source, the selected image, and the image synthesis method from the emphasis mode storage according to the emphasis mode received; and control the image processor according to the drive pattern, the selected image, the image synthesis method read from the emphasis mode storage to cause the image processor to generate the first primary intermediate emphasis image signal.

23. The endoscope apparatus according to claim 22, wherein the plurality of emphasis modes comprises:
   a first emphasis mode to display a first intermediate emphasis image that is an intermediate emphasis image of the diagnosis target substance in at least a specific depth region, and
   a second emphasis mode to display a second intermediate emphasis image that is an intermediate emphasis image of the diagnosis target substance in a depth region different from that of the first intermediate emphasis image.

* * * * *